(12) United States Patent
Abbas et al.

(10) Patent No.: US 8,513,300 B2
(45) Date of Patent: Aug. 20, 2013

(54) FORMULATIONS FOR ORAL ADMINISTRATION OF CROMOLYN SODIUM

(75) Inventors: Richat Abbas, Mohegan Lake, NY (US); Ehud Arbit, Tarrytown, NY (US); Michael Goldberg, Tarrytown, NY (US); Vivien Wong, Tarrytown, NY (US); Donald J. Sarubbi, Bolton, MA (US)

(73) Assignee: Emisphere Technologies, Inc., Roseland, NJ (US)

( * ) Notice: Subject to any disclaimer, the term of this patent is extended or adjusted under 35 U.S.C. 154(b) by 217 days.

(21) Appl. No.: 12/103,821

(22) Filed: Apr. 16, 2008

(65) Prior Publication Data

US 2008/0194676 A1    Aug. 14, 2008

Related U.S. Application Data

(62) Division of application No. 10/497,286, filed as application No. PCT/US02/38247 on Nov. 29, 2002, now abandoned.

(60) Provisional application No. 60/334,395, filed on Nov. 29, 2001, provisional application No. 60/384,916, filed on May 24, 2002.

(51) Int. Cl.
*A01N 43/16* (2006.01)
*A61K 31/35* (2006.01)

(52) U.S. Cl.
USPC ............ 514/451; 514/183; 514/449; 424/400

(58) Field of Classification Search
USPC .......................................................... 514/183
See application file for complete search history.

(56) References Cited

U.S. PATENT DOCUMENTS

| | | | |
|---|---|---|---|
| 5,650,386 A * | 7/1997 | Leone-Bay et al. | ............... 514/2 |
| 5,958,407 A * | 9/1999 | Bunnett et al. | ............. 424/94.64 |
| 2002/0028193 A1* | 3/2002 | Cornett et al. | ............. 424/93.21 |
| 2002/0037846 A1* | 3/2002 | Cadieux | .......................... 514/12 |

FOREIGN PATENT DOCUMENTS

| | | |
|---|---|---|
| CA | 2188467 | 2/1995 |
| CA | 2214323 | 3/1996 |
| CA | 2369591 | 12/2000 |
| JP | 6281380 | 10/1994 |
| JP | 08509474 | 10/1996 |
| JP | 09504300 | 4/1997 |
| JP | 10507762 T | 7/1998 |
| JP | 2001513080 T | 8/2001 |
| JP | 2001524109 T | 11/2001 |
| WO | WO-9423767 A1 | 10/1994 |
| WO | WO 95/28838 | 2/1995 |
| WO | WO-9511690 A1 | 5/1995 |
| WO | WO-9612473 A1 | 5/1996 |
| WO | WO-9630036 A1 | 10/1996 |
| WO | WO 98/08504 | 3/1998 |
| WO | WO-9834632 A1 | 8/1998 |
| WO | WO-9849135 A1 | 11/1998 |
| WO | WO-9936060 A1 | 7/1999 |
| WO | WO-0006534 A1 | 2/2000 |
| WO | WO-0007979 A2 | 2/2000 |
| WO | WO-0027392 A1 | 5/2000 |
| WO | WO-0050386 A1 | 8/2000 |
| WO | WO 00/59863 | 10/2000 |
| WO | WO 00/59863 | 12/2000 |
| WO | WO-0132130 A2 | 5/2001 |
| WO | WO-0144199 A1 | 6/2001 |
| WO | WO-0151454 A1 | 7/2001 |
| WO | WO-0202509 A1 | 1/2002 |
| WO | WO-0220466 A1 | 3/2002 |

OTHER PUBLICATIONS

Selvaraj et al., 2005, Biol. Pharm. Bull., vol. 28, No. 11, pp. 2128-2132.*
Leone-Bay et al., "Oral Delivery of Sodium Cromolyn: Preliminary Studies in Vivo and in Vitro", Pharmaceutical Research, vol. 13, No. 2, pp. 222-226, 1996.

* cited by examiner

*Primary Examiner* — Jeffrey S. Lundgren
*Assistant Examiner* — Meghan Finn
(74) *Attorney, Agent, or Firm* — Blank Rome LLP

(57) ABSTRACT

An oral dosage form comprises cromolyn sodium (sodium or disodium cromoglycate), and an acylated amino acid delivery agent.

28 Claims, 12 Drawing Sheets

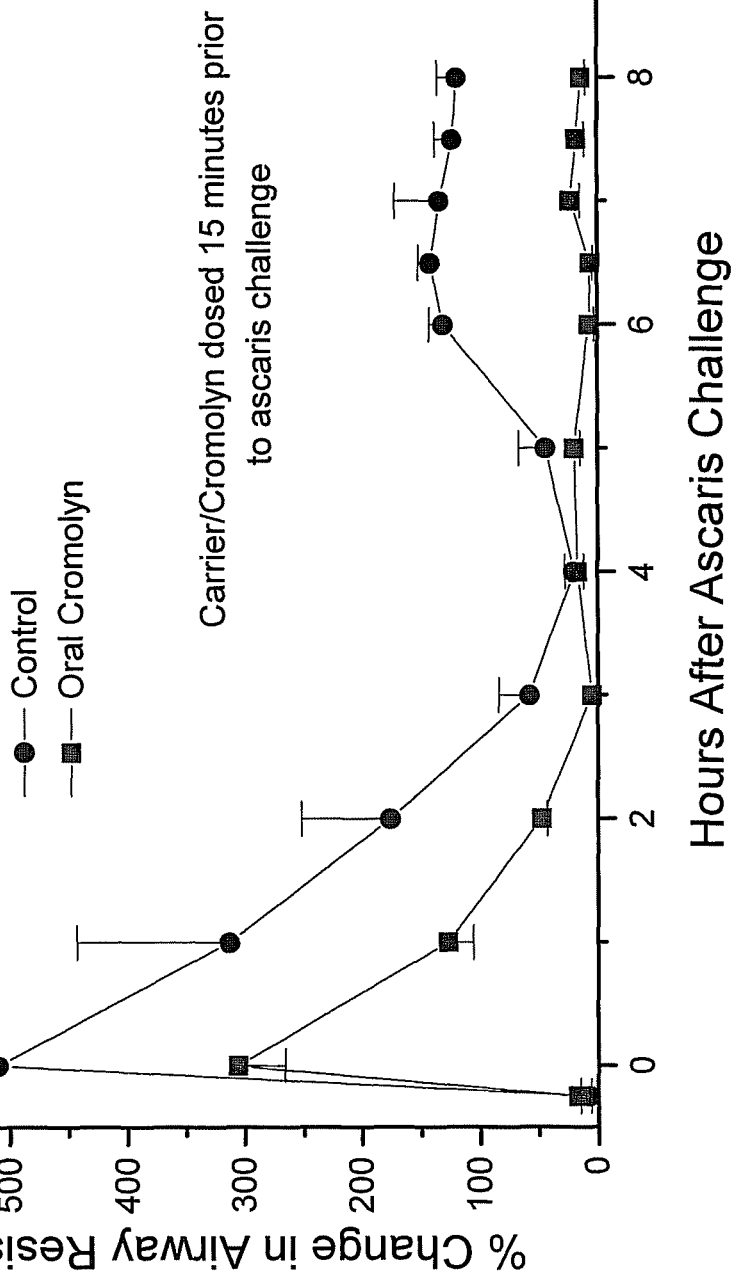

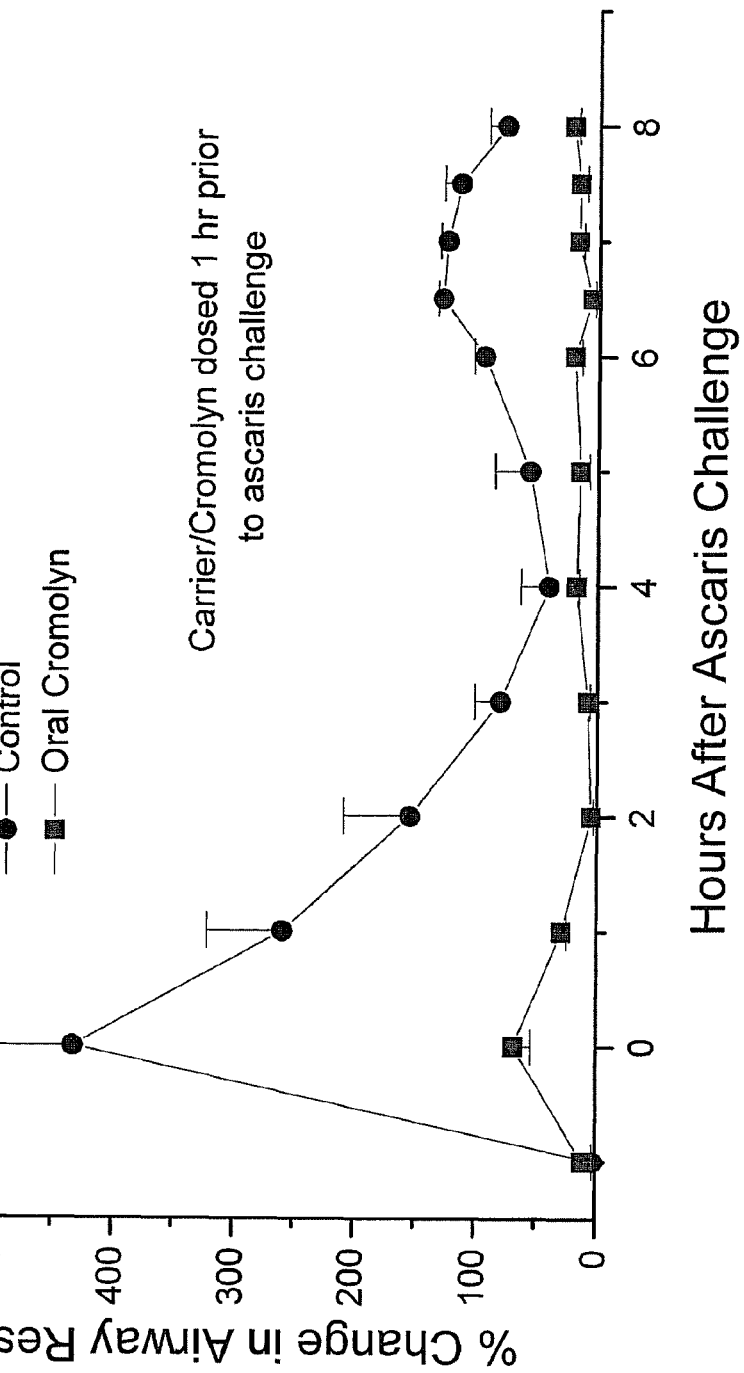

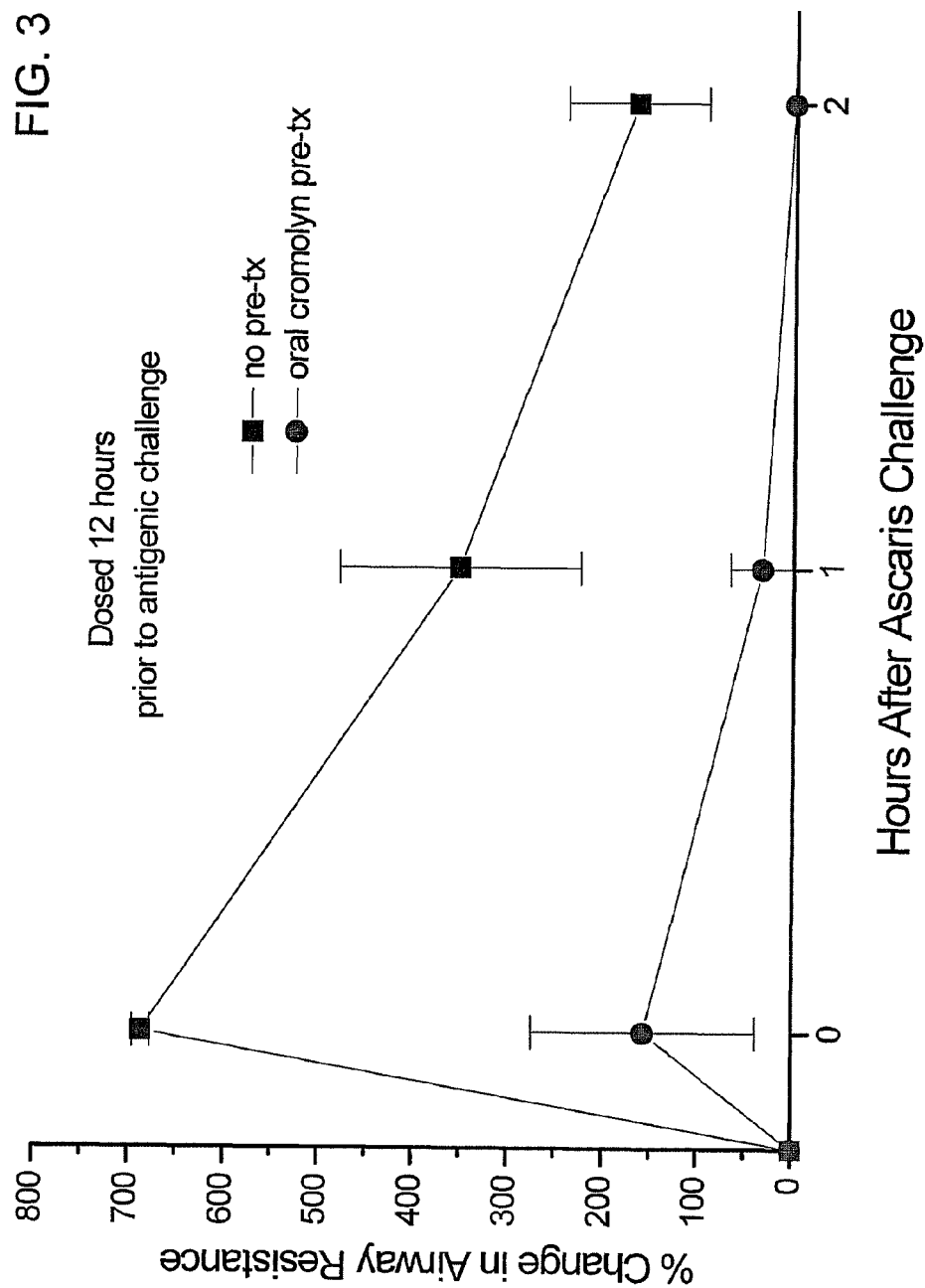

Figure 4: Treatment Group 1 (40 mg Cromolyn/1200 mg SNAC) Cromolyn Concentrations (ng/mL) in Human Plasma

| Sample ID | Time, h | S001 | S002 | S003 | S004 | S005 | S006 | S007 | S008 | S009 | S010 |
|---|---|---|---|---|---|---|---|---|---|---|---|
| P0 | 0.000 | bql | bql | bql | bql | bql | bql | bql | bql | bql | bql |
| P1 | 0.083 | bql | bql | bql | bql | bql | 0.566 | bql | bql | bql | bql |
| P2 | 0.167 | 1.54 | 6.00 | 0.818 | 0.614 | 9.33 | 7.16 | bql | bql | bql | bql |
| P3 | 0.250 | 8.73 | 26.87 | 16.01 | 7.44 | 28.48 | 29.32 | 2.93 | 7.55 | bql | bql |
| P4 | 0.333 | 13.16 | 41.79 | 24.00 | 13.66 | 32.31 | 32.13 | 5.66 | 15.72 | bql | 0.325 |
| P5 | 0.500 | 8.77 | 31.66 | 16.71 | 9.81 | 21.26 | 21.33 | 5.15 | 10.87 | 0.780 | 0.696 |
| P6 | 0.750 | 5.31 | 22.12 | 11.86 | 5.50 | 11.35 | 10.62 | 4.10 | 6.21 | 1.10 | 0.930 |
| P7 | 1.00 | 4.07 | 14.62 | 6.78 | 3.12 | 8.59 | 6.18 | 2.92 | 3.76 | 0.963 | 0.836 |
| P8 | 1.25 | 2.48 | 9.99 | 4.98 | 1.99 | 5.81 | 4.44 | 1.72 | 2.58 | 1.31 | 1.46 |
| P9 | 1.50 | 2.01 | 5.94 | 3.71 | 1.18 | 3.89 | 2.55 | 2.36 | 1.75 | 1.16 | 2.64 |
| P10 | 2.00 | 1.02 | 3.02 | 1.50 | 0.879 | 1.83 | 1.43 | 1.82 | 0.928 | 1.30 | 2.94 |
| P11 | 2.50 | 0.723 | 2.15 | 0.863 | 0.453 | 0.661 | 0.948 | 0.884 | 0.771 | 1.26 | 1.99 |
| P12 | 3.00 | 0.430 | 1.47 | 0.407 | bql | 0.584 | 0.636 | 0.659 | 0.570 | 1.71 | 1.24 |
| P13 | 4.00 | bql | 0.624 | bql | bql | 0.392 | 0.538 | 0.593 | 0.490 | 0.692 | 0.500 |
| P14 | 6.00 | bql | bql | 0.554 | 1.13 | bql | 0.484 | bql | 0.463 | 1.01 | 0.535 |
| P15 | 8.00 | bql | bql | 0.343 | 0.616 | 0.356 | 0.682 | 0.451 | bql | 0.724 | 0.946 | bql: < 0.3125 ng/mL
NC: Not Calculated
Run Numbers: 011108-S06, 011108-S07, and 011109-S09

Figure 5: Treatment Group 2 (80 mg Cromolyn/1200 mg SNAC) Cromolyn Concentrations (ng/mL) in Human Plasma

| Sample ID | Time, h | Subject |  |  |  |  |  |  |  |  |  |
|---|---|---|---|---|---|---|---|---|---|---|---|
|  |  | S001 | S002 | S003 | S004 | S005 | S006 | S007 | S008 | S009 | S010 |
| P0  | 0.000 | bql   | bql   | bql   | bql   | bql   | bql   | bql   | bql   | bql | bql |
| P1  | 0.083 | bql   | bql   | bql   | bql   | bql   | bql   | bql   | bql   | bql | bql |
| P2  | 0.167 | 1.34  | 1.10  | 1.06  | bql   | 9.26  | 8.10  | bql   | bql   | bql | bql |
| P3  | 0.250 | 9.22  | 47.82 | 31.62 | 15.62 | 57.58 | 46.96 | 12.42 | 12.62 | bql | bql |
| P4  | 0.333 | 19.52 | 75.16 | 40.16 | 32.40 | 80.12 | 46.72 | 35.24 | 19.74 | bql | bql |
| P5  | 0.500 | 12.08 | 49.84 | 37.22 | 26.40 | 52.62 | 29.02 | 31.10 | 13.92 | bql | bql |
| P6  | 0.750 | 6.36  | 31.76 | 21.56 | 15.54 | 28.84 | 14.54 | 18.42 | 8.26  | bql | bql |
| P7  | 1.00  | 4.72  | 22.44 | 14.10 | 12.68 | 16.74 | 9.00  | 10.78 | 4.12  | bql | bql |
| P8  | 1.25  | 2.92  | 14.78 | 11.38 | 9.98  | 10.50 | 6.26  | 6.70  | 3.26  | bql | bql |
| P9  | 1.50  | 2.04  | 9.40  | 7.90  | 5.98  | 7.08  | 5.14  | 4.66  | 2.30  | bql | bql |
| P10 | 2.00  | 1.06  | 5.76  | 5.06  | 3.16  | 3.88  | 3.68  | 2.42  | 1.24  | bql | bql |
| P11 | 2.50  | 0.632 | 3.46  | 2.28  | 1.67  | 2.12  | 1.47  | 1.09  | 0.746 | bql | bql |
| P12 | 3.00  | bql   | 2.76  | 2.04  | 0.686 | 1.59  | 1.18  | 0.904 | 0.890 | bql | bql |
| P13 | 4.00  | bql   | 1.51  | 0.866 | bql   | 0.802 | 0.710 | 0.616 | 0.450 | bql | bql |
| P14 | 6.00  | 0.862 | 0.782 | 2.22  | 1.44  | 0.514 | 0.812 | 0.596 | 0.570 | bql | bql |
| P15 | 8.00  | bql   | bql   | 3.24  | 1.21  | 0.716 | 0.658 | bql   | bql   | bql | bql | bql: < 0.3125 ng/mL
NC: Not Calculated
Run Numbers: 011106-S04 and 011107-S05-r

Figure 6: Treatment Group 3 (80 mg Cromolyn/600 mg SNAC) Cromolyn Concentrations (ng/mL) in Human Plasma

| Sample ID | Time, h | Subject | | | | | | | |
|---|---|---|---|---|---|---|---|---|---|
| | | S001 | S002 | S003 | S004 | S005 | S006 | S007 | S008 |
| P0 | 0 | bql | bql | bql | bql | bql | bql | bql | bql |
| P1 | 0.083 | bql | bql | bql | bql | bql | bql | bql | bql |
| P2 | 0.167 | bql | bql | 30.22 | 0.700 | 16.34 | 8.40 | 2.14 | 1.26 |
| P3 | 0.25 | 16.60 | 26.62 | 64.76 | 11.90 | 29.44 | 40.76 | 16.20 | 41.56 |
| P4 | 0.333 | 27.30 | 53.32 | 100.9 | 36.50 | 30.10 | 52.56 | 24.66 | 40.28 |
| P5 | 0.5 | 21.50 | 40.10 | 62.46 | 29.60 | 16.82 | 25.66 | 19.16 | 26.60 |
| P6 | 0.75 | 11.32 | 19.76 | 29.02 | 15.26 | 10.22 | 14.80 | 10.76 | 16.76 |
| P7 | 1 | 9.34 | 14.78 | 15.20 | 12.94 | 7.06 | 8.30 | 13.16 | 9.92 |
| P8 | 1.25 | 6.58 | 14.08 | 21.23 | 10.13 | 5.71 | 5.18 | 6.06 | 5.11 |
| P9 | 1.50 | 4.45 | 9.25 | 11.61 | 7.24 | 4.10 | 4.10 | 3.89 | 3.68 |
| P10 | 2.00 | 2.46 | 5.07 | 5.98 | 5.11 | 2.32 | 1.99 | 2.06 | 1.97 |
| P11 | 2.50 | 1.25 | 3.00 | 3.12 | 4.13 | 1.38 | 1.05 | 0.990 | 1.38 |
| P12 | 3.00 | 1.01 | 2.07 | 1.77 | 3.05 | 0.954 | 1.15 | 0.903 | 0.917 |
| P13 | 4.00 | 0.406 | 1.03 | 1.93 | 1.22 | 0.672 | 0.701 | 0.538 | 0.719 |
| P14 | 6.00 | 0.839 | 0.567 | 1.86 | 1.23 | 0.495 | 0.423 | 0.600 | 0.546 |
| P15 | 8.00 | 0.399 | bql | 1.01 | 0.906 | 1.06 | 0.359 | 0.445 | 0.437 | bql: < 0.3125 ng/mL
NC: Not Calculated
Run Numbers: 011103-S03 and 011111-S10

Figure 7: Treatment Group 4 (120 mg Cromolyn/200 mg SNAC) Cromolyn Concentrations (ng/mL) in Human Plasma

| Sample ID | Time, h | Subject | | | | | | | |
|---|---|---|---|---|---|---|---|---|---|
| | | S001* | S002 | S003 | S004 | S005* | S006* | S007 | S008 |
| P0 | 0.000 | bql | bql | bql | bql | bql | bql | bql | bql |
| P1 | 0.083 | 0.374 | bql | 1.02 | bql | 3.67 | 0.333 | bql | bql |
| P2 | 0.167 | 2.90 | 1.00 | 1.90 | 0.551 | 7.28 | bql | 1.90 | 3.72 |
| P3 | 0.250 | 11.11 | 82.26 | 1.73 | 10.46 | 41.48 | 3.50 | 5.10 | 12.61 |
| P4 | 0.333 | 29.59 | 85.90 | 2.18 | 46.05 | 45.16 | 26.54 | 5.57 | 13.22 |
| P5 | 0.500 | 36.07 | 55.25 | 2.74 | 54.53 | 29.30 | 13.46 | 5.73 | 7.85 |
| P6 | 0.750 | 28.46 | 27.32 | 3.38 | 31.78 | 14.05 | 8.50 | 4.02 | 5.46 |
| P7 | 1.00 | 19.53 | 15.75 | 3.14 | 17.70 | 10.93 | 5.72 | 3.82 | 3.01 |
| P8 | 1.25 | 13.74 | 11.39 | 2.86 | 12.77 | 7.35 | 5.55 | 3.14 | 1.87 |
| P9 | 1.50 | 10.05 | 8.11 | 2.66 | 10.86 | 5.30 | 4.24 | 2.15 | 1.48 |
| P10 | 2.00 | 7.00 | 9.90 | 2.80 | 8.01 | 3.02 | 2.50 | 1.38 | 0.941 |
| P11 | 2.50 | 5.90 | 4.25 | 3.08 | 7.18 | 1.60 | 1.49 | 1.15 | 0.694 |
| P12 | 3.00 | 3.67 | 6.21 | 2.47 | 5.54 | 1.30 | 1.48 | 0.760 | 0.606 |
| P13 | 4.00 | 2.87 | 6.11 | 2.78 | 2.71 | 0.943 | 0.928 | 0.963 | 0.861 |
| P14 | 6.00 | 2.25 | 1.76 | 2.84 | 2.05 | 0.524 | 0.485 | 0.686 | 1.44 |
| P15 | 8.00 | 1.25 | 0.461 | 2.18 | 1.26 | 0.849 | 0.522 | 0.895 | 0.912 | bql: < 0.3125 ng/mL
NC: Not Calculated
Run Numbers: 011109-S08 and 011109-S09
* The 0 and 0.083 h samples were switched during initial sample processing and confirmed by reassay

FORMULATIONS FOR ORAL ADMINISTRATION OF CROMOLYN SODIUM

CROSS REFERENCE TO RELATED APPLICATION

This application is a divisional of U.S. patent application Ser. No. 10/497,286, filed May 28, 2004 now abandoned as a national phase application under 35 U.S.C. §371 of International Patent Application No. PCT/US02/38247, filed Nov. 29, 2002, and claimed the benefit under 35 U.S.C. §119(e) of U.S. Provisional Patent Application No. 60/334,395, filed Nov. 29, 2001, and No. 60/384,916, filed May 24, 2002.

TECHNICAL FIELD OF THE INVENTION

This invention relates to delivery of therapeutic polar organic compounds in a bioavailable and bioactive form. This invention further relates to oral administration of polar organic compounds as active agents as part of a therapeutic regimen. This invention further relates to the oral administration of cromolyn in a bioavailable and bioactive form for the treatment of asthma, allergies and viral infections.

This invention is directed to formulations of a delivery agent and cromolyn for oral administration. This invention further relates to formulations of a delivery agent and cromolyn for oral administration that releases cromolyn which is both bioavailable and bioactive for the treatment of asthma, allergies and viral infections.

This invention relates to providing methods for the granulation and encapsulation of a formulation comprising a delivery agent and cromolyn for oral administration. This invention further relates to providing methods for the granulation and encapsulation of a formulation comprising a absorption agent molecule and cromolyn for oral administration that releases cromolyn which is both bioavailable and bioactive for the treatment of allergies and asthma.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically or chemically active agents are particularly vulnerable to such barriers. For example in the delivery to humans and animals of pharmacological and therapeutic agents, barriers are imposed by the body. Examples of physical barriers are the skin and various organ membranes that must be traversed before reaching a target. Chemical barriers include, but are not limited to, pH variations, lipid bilayers, and degrading enzymes. These barriers are of particular significance in the design of oral delivery systems. Oral delivery of many biologically or chemically active agents would be the route of choice for administration to humans and animals if not for biological, chemical, and physical barriers such as varying pH in the gastro-intestinal (GI) tract, powerful digestive enzymes, and active agent impermeable gastro-intestinal membranes. Among the numerous agents which are not typically amenable to oral administration are biologically or chemically polar organic compounds, such as cromolyn, antibiotics and other organic substances. These agents are rapidly rendered partially or totally ineffective, pass through partially or totally unabsorbed, or are partially or totally destroyed in the gastro-intestinal tract by acid hydrolysis, enzymes, or the like.

Earlier methods for orally administering vulnerable pharmacological agents, such as polar organic compounds and biological macromolecules have relied on the co-administration of adjuvants (e.g., resorcinols and non-ionic surfactants such as polyoxyethylene oleyl ether and n-hexadecylpolyethylene ether) to artificially increase the permeability of the intestinal walls, as well as the co-administration of enzymatic inhibitors (e.g., pancreatic trypsin inhibitors, diisopropylfluorophosphate (DFF) and aprotinin) to inhibit enzymatic degradation.

The oral administration of therapeutic agents that require parenteral administration would greatly improve patient compliance and reduce the costs and risks associated with injections. Absorption of drugs via the gastrointestinal (GI) tract, however, is hampered by natural barriers including acid-induced hydrolysis in the stomach, enzymatic degradation throughout the GI tract, poor solubility in the intestinal environment, and lack of permeation through the epithelial cells. The latter is particularly problematic because it can exclude the passage of compounds across the tissue based on size, charge and/or lipophilicity. A common strategy to overcome this obstacle is the use of general penetration enhancers and/or nonspecific protease inhibitors. These systems, however, are highly inefficient and have been shown to cause transient to long-lasting membrane damage. Such membrane effects have the added disadvantage of allowing nonselective transport of toxic materials.

In current practice, cromolyn sodium is used by inhalation as a prophylactic agent in the treatment of mild to moderate asthma, as a nasal inhaler to treat seasonal bronchial asthma and as an ophthalmic solution to treat allergic or vernal conjunctivitis. Cromolyn is a mast cell stabilizer and as such attacks the initial step in the cascade that results in the manifestation of allergy including asthma and allergic rhinitis. The mechanism of action of cromolyn is through inhibiting the release of histamine and leukotrienes from the mast cells. Cromolyn has a high safety profile but exhibits poor absorption from the gastrointestinal tract. The clinical practicality and patient compliance of this drug is reduced because it is available mainly as an inhalation agent, and several weeks of therapy may be required before improvement is apparent. Cromolyn, when given orally, is poorly absorbed from the gastrointestinal tract because it is highly lipid-insoluble and mainly ionized.

Cromolyn is available only as an inhalation agent, except for an oral concentrate commercially available in the United States under the trade name Gastrocrom® from Celltech Pharmaceuticals, Inc. Gastrocrom® is provided in 5 ml ampoules containing 100 mg cromolyn sodium, USP, in purified water. Gastrocrom® is indicated in the management of patients with mastocytosis, and use of this product is said to be associated with improvement in diarrhea, flushing, headaches, vomiting, uticaria, abdominal pain, nausea and itching in some patients. No more than 1% of an administered dose of Gastrocrom® is absorbed by humans after oral administration (Physician's Desk Reference® 2001, page 1840-1841).

Many investigators believe that if cromolyn were to be available in an oral form and with good absorption from the gastrointestinal tract, it would become a valuable addition with broad application in the treatment of allergic asthma and rhinitis.

OBJECTS OF THE INVENTION

It is an object of the present invention to provide polar organic compounds in an orally bioavailable and bioactive form.

It is an object of the present invention to provide cromolyn in a bioavailable and bioactive form.

It is also an object of the present invention to provide bioavailable cromolyn as an active agent as part of a therapeutic regimen.

It is another object of the present invention to provide formulations of a delivery agent and cromolyn for oral administration.

It is still another object of the present invention to provide formulations of a delivery agent and cromolyn for oral administration that provides cromolyn in a form which is both bioavailable and bioactive for the treatment of allergies and asthma.

It is yet another object of the present invention to provide methods for the granulation and encapsulation of a formulation comprising a delivery agent and cromolyn for oral administration.

It is a further object of the present invention to provide cromolyn sodium in an oral dosage form for the treatment of any inflammatory process involving the release of cytokines and/or histamine from mast cells.

It is still a further object of the present invention to provide an oral dosage form of cromolyn sodium suitable for the treatment of inflammatory diseases.

It is yet a further object of the present invention to provide an oral dosage form of cromolyn sodium suitable for the prophylactic treatment of allergies including allergic rhinitis, asthma, rheumatoid arthritis, etc.

SUMMARY OF THE INVENTION

The following terms will be used throughout the application as defined below:

Effective amount of drug—an amount of the drug (e.g., cromolyn sodium) that is effective to treat or prevent a condition in a living organism to whom it is administered over some period of time, e.g., provides a therapeutic effect during a desired dosing interval.

Effective amount of delivery agent—an amount of the delivery agent that promotes the absorption of a desired amount of the drug from the gastrointestinal tract.

Organic solvents—any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alcohol, toluene, carbon tetrachloride, or combinations thereof.

Patient—refers to any animal that is to be treated with the formulations and compositions by the methods herein disclosed.

Peptide—a polypeptide of small to intermediate molecular weight, usually 2 or more amino acid residues and frequently but not necessarily representing a fragment of a larger protein.

Protein—a complex high polymer containing carbon, hydrogen, oxygen, nitrogen and usually sulfur and composed of chains of amino acids connected by peptide linkages. Proteins in this application refer to glycoproteins, antibodies, non-enzyme proteins, enzymes, hormones and peptides. The molecular weight range for proteins includes peptides of 1000 Daltons to glycoproteins of 600 to 1000 kiloDaltons.

Prophylactically effective amount—an amount of a formulation or composition which is effective to prevent or reduce the incidence or severity of a condition in a living organism to whom it is administered over some period of time.

Reconstitution—dissolution of formulations or compositions in an appropriate buffer or pharmaceutical formulation.

Shelf stability—the loss of specific activity that results in decreased activity over time incubated under specified conditions.

Unit-Dose Forms—refers to physically discrete units suitable for human and animal subjects and packaged individually as is known in the art. It is contemplated for purposes of the present invention that dosage forms of the present invention comprising therapeutically effective amounts of cromolyn may include one or more unit doses (e.g., tablets, capsules) to achieve the therapeutic effect.

The term "therapeutically effective" as is used herein refers to the release of drug from the dosage form and the absorption of the drug to an extent at which blood (e.g., plasma) concentrations (levels) of the drug (e.g., cromolyn) are maintained within the therapeutic range (above the minimum effective concentration or "MEC") but below toxic levels over the dosing interval.

The term "$C_{max}$" as is used herein means the highest plasma concentration of the drug attained within the dosing interval.

The term "$T_{max}$" as is used herein means the time period that elapses after administration of the dosage form at which the plasma concentration of the drug attains the $C_{max}$ within the dosing interval.

The term "$K_{el}$" as is used herein means the terminal elimination rate constant calculated by linear regression of the terminal linear portion of the log concentration vs. time curve.

The term "$\lambda_t$" as is used herein means the terminal elimination rate constant.

The term "AUC" as used herein means area under the plasma concentration-time curve, as calculated by the trapezoidal rule over the complete dosing interval, e.g., 24-hour interval.

The term "$AUC_{(0-t)}$" as used herein means the area under the plasma concentration-time curve using linear trapezoidal summation from time zero to time t post-dose, where t is the time of the last measurable concentration ($C_t$).

The term "$AUC_{(0-inf)}$" as used herein means the area under the plasma concentration-time curve from time 0 to infinity, $AUC_{(0-inf)}=AUC_{(0-t)}+C_t/K_c$.

The term "single dose" means that the human patient has received a single dose of the drug formulation and the drug plasma concentration has not achieved steady state.

The term "multiple dose" means that the human patient has received at least two doses of the drug formulation in accordance with the dosing interval for that formulation.

Unless specifically designated as "single dose" or at "steady-state" the pharmacokinetic parameters disclosed and claimed herein encompass both single dose and steady-state conditions.

The term "mean", when preceding a pharmacokinetic value (e.g., mean $T_{max}$) represents the arithmetic mean value of the pharmacokinetic value unless otherwise specified.

The term "CL/F" as used herein means the apparent total body clearance calculated as Dose/$AUC_{(0-inf)}$.

The term "MRT" as used herein means the mean residence time calculated as the ratio of the Area Under the first moment of the plasma concentration-time curve (AUMC) and the area under the plasma concentration-time curve, (AUMC)/$AUC_{(0-inf)}$.

The term "$T_{1/2}$" as used herein means the terminal half-life calculated as $\ln(2)/K_{el}$.

The term "$T_{1/2}(\lambda_t)$" as used herein means the terminal elimination half life of the drug.

The term "$V_d/F$" as used herein means the apparent volume of distribution calculated as $(CL/F)/K_{el}$.

The term "% Extr." as used herein means the percentage of $AUC_{0-inf}$ extrapolated to infinity.

The term "γ-GTP" as used herein means Gamma-Glutamyl Transpeptidase.

The term "PNIF" as used herein means the Peak Nasal Inspiratory Flow.

As used herein and in the appended claims, the singular forms "a," "an," and "the" include plural referents unless the context clearly indicates otherwise. In addition, reference to "the method" includes reference to equivalent steps and methods known to those of ordinary skill in the art that could be modified or substituted for the methods described herein.

In accordance with the above and other objects, the present invention is related in part to oral dosage forms comprising a polar organic compound, particularly cromolyn sodium, and a delivery agent or salts thereof in an effective amount to provide good absorption of cromolyn from the gastrointestinal tract.

More particularly, the present invention is related in part to an oral dosage form comprising cromolyn sodium (sodium or disodium cromoglycate) and a delivery agent in an amount effective to provide an absorption of cromolyn from the gastrointestinal tract of greater than about 2% of the dose of cromolyn contained in the dosage form, by weight, said formulation containing an amount of said cromolyn sodium necessary to render a therapeutic effect.

The invention is further related to an oral dosage form comprising cromolyn sodium and a pharmaceutically acceptable delivery agent in an effective amount to provide therapeutically effective blood plasma levels of cromolyn upon oral administration, said dosage form providing a $T_{max}$ of cromolyn in less than about 1 hour, and in certain embodiments preferably at from about 0.2 to about 0.5 hours after oral administration.

The invention is further related to an oral dosage form comprising cromolyn sodium and a pharmaceutically acceptable delivery agent in an effective amount to provide therapeutically effective blood plasma levels of cromolyn upon oral administration, the dosage form providing a $C_{max}$ of cromolyn from about 10 ng/ml to about 1700 ng/ml. In one embodiment of the present invention, the dosage form provides a $C_{max}$ of cromolyn from about 22.3 ng/ml to about 200 ng/ml. In another embodiment of the present invention, the dosage form provides a $C_{max}$ of cromolyn from about 20 ng/ml to about 100 ng/ml. In still another embodiment of the present invention, the dosage form provides a $C_{max}$ of cromolyn from about 25 ng/ml to about 80 ng/ml. In yet another embodiment of the present invention, the dosage form provides a $C_{max}$ of cromolyn from about 40 ng/ml to about 60 ng/ml.

The invention is further related to an oral dosage form comprising cromolyn sodium and a pharmaceutically acceptable absorption enhancing delivery agent in an effective amount to provide a $T_{max}$ of cromolyn after oral administration of the dosage form at from about 0.2 to about 0.5 hours after oral administration, and a $C_{max}$ of cromolyn from about 10 ng/ml to about 1700 ng/ml, and in certain embodiments from about 4 ng/ml to about 250 ng/ml.

In certain embodiments of the invention, the oral dosage form described herein provides a mean plasma level of cromolyn from about 4 ng/ml to about 250 ng/ml during a dosage interval. In other embodiments, the oral dosage form provides a mean plasma level of cromolyn from about 10 ng/ml to about 60 ng/ml during a dosage interval. In yet other embodiments, the oral dosage form provides a mean plasma level of cromolyn from about 30 ng/ml to about 60 ng/ml during a dosage interval.

In certain embodiments of the invention, the oral dosage form described herein provides a mean $C_{max}$ from about 10 ng/ml to about 250 ng/ml.

In certain embodiments of the invention, the oral dosage form contains from about 40 mg to about 1 gram cromolyn sodium (either in one unit dose or in multiple unit doses, e.g., tablets or capsules), in certain embodiments the oral dosage form contains from about 40 mg to about 800 mg cromolyn sodium, and in other embodiments the oral dosage form contains from 240 mg cromolyn sodium; and further contains from about 100 mg to about 2500 mg delivery agent (either in one unit dose or in multiple unit doses, e.g., tablets or capsules), and in certain embodiments contains from about 200 mg to about 1200 mg delivery agent. In certain preferred embodiments, the delivery agent is included in the dosage form in an amount from about 200 to about 800 mg. In yet other embodiments, the delivery agent is included in the dosage form in an amount of about 500 mg to about 700 mg.

Alternatively, and in accordance with the methods of the invention, the delivery agent in that same amount may be separately administered to the animal in need of treatment.

In certain embodiments of the invention, the delivery agent used in the oral dosage form and methods described herein has the formula or salts thereof:

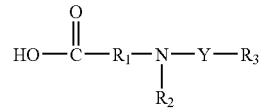

wherein Y is carbonyl (CO) or $SO_2$; $R_1$ is $C_3$-$C_{24}$ alkyl, $C_2$-$C_{20}$ alkenyl, $C_2$-$C_{20}$ alkyne, cycloalkyl, or aromatic; $R_2$ is hydrogen, $C_1$-$C_4$ alkyl, or $C_2$-$C_4$ alkenyl; and $R_3$ is $C_1$-$C_7$ alkyl, $C_3$-$C_{10}$ cycloalkyl, aryl, thienyl, pyrrolo, or pyridyl, where $R_3$ is optionally substituted by one or more $C_1$-$C_5$ alkyl group, $C_2$-$C_4$ alkenyl group, halogen preferably For Cl, OH, $SO_2$, COOH, or $SO_3H$.

In a preferred embodiment, $R_1$ is $C_3$-$C_{12}$ alkyl, more preferably $C_3$-$C_9$ alkyl, more preferably $C_5$-$C_7$ alkyl, more preferably $C_7$ alkyl.

In a preferred embodiment, $R_3$ is 2OH substituted phenyl or preferably 2OH substituted phenyl further substituted with a halogen such as F, or Cl.

In other preferred embodiments, the delivery agent used in the oral dosage form and methods described herein has the formula or salts thereof:

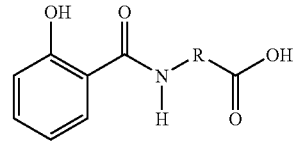

wherein R is $C_3$-$C_{24}$ alkyl, $C_2$-$C_{20}$ alkenyl, $C_2$-$C_{20}$ alkyne, cycloalkyl, or aromatic.

In certain preferred embodiments of the invention, the delivery agent is Sodium N-[8-(2-hydroxybenzoyl)amino] caprylate (SNAC) or salts thereof.

In certain embodiments, the cromolyn sodium and the delivery agent are simultaneously administered. In other embodiments, the cromolyn sodium and the delivery agent are sequentially administered.

In certain preferred embodiments, the delivery agent is in an amount effective to provide an absorption of cromolyn from the gastrointestinal tract of greater than about 3.5% of the dose of cromolyn contained in the dosage form.

Also contemplated is a method for preparing these compositions which comprises mixing at least one biologically active agent with at least one delivery agent as described above and, optionally, a dosing vehicle (e.g., pharmaceutical excipients).

In an alternative embodiment, these non-toxic delivery agents are orally administered to animals as part of a delivery system by blending or mixing the delivery agent(s) with the biologically active agent prior to administration. Also contemplated by the present invention are dosage unit forms that include these compositions.

According to the invention, modified amino acids are prepared by reacting single amino acids or mixture of two or more kinds of amino acids with an acylating or sulfonating agent which reacts with free amino moieties present in the amino acids to form amides or sulfonamides, respectively. The modified amino acids are then recovered from the mixture.

The modified amino acids are non-toxic and can be orally administered to mammals as a drug delivery system by simply mixing the modified amino acids with an active agent prior to administration. Alternatively, the drug and the delivery agent may be sequentially administered.

In certain embodiments, the invention provides an oral dosage form comprising a dose of cromolyn sodium and a delivery agent that upon oral administration provides a systemic absorption of the cromolyn sodium in an amount effective to inhibit the release of histamine and/or cytokines from mast cells. The delivery agent could comprise sodium N-[8-(2-hydroxybenzoyl)amino]caprylate (SNAC) in a ratio from about 1:30 to about 3:4 (weight/weight).

In other embodiments, the invention provides an oral dosage form comprising cromolyn sodium (sodium or disodium cromoglycate), and an acylated amino acid delivery agent in an amount effective to provide an absorption of cromolyn from the gastrointestinal tract of greater than about 2% of the dose of cromolyn contained in the dosage form, by weight, said formulation containing an amount of said cromolyn sodium necessary to render a systemic therapeutic effect.

In certain embodiments, the oral dosage form is solid. The oral dosage form could alternatively be in the form of a tablet, capsule or oral suspension. In certain embodiments, the oral dosage form is suitable for being administered once a day, twice a day, three times a day or four times a day.

In certain embodiments, the oral dosage form comprises a dose of cromolyn sodium of from about 40 mg to about 240 mg. In certain other embodiments, the oral dosage form comprises a dose of cromolyn sodium of from about 50 mg to about 100 mg.

In certain embodiments, the oral dosage form comprises a dose of the delivery agent of from about 100 mg to about 1200 mg. In certain other embodiments, the oral dosage form comprises a dose of the delivery agent of from about 200 mg to about 800 mg.

In certain embodiments, the oral dosage form provides a $T_{max}$ for cromolyn sodium at about 0.1 to about 1.5 hours after oral administration. In certain other embodiments, the oral dosage form provides a $T_{max}$ for cromolyn sodium at about 0.2 to about 0.5 hours after administration.

In certain embodiments, the oral dosage form provides an AUC for cromolyn sodium of between about 15 and about 60 ng·h/mL. In certain other embodiments, the oral dosage form provides an AUC for cromolyn sodium of between about 30 and about 40 ng·h/mL.

In certain embodiments, the oral dosage form provides a mean plasma level of cromolyn from about 4 ng/ml to about 1700 ng/ml during a dosage interval. In certain other embodiments, the oral dosage form provides a mean plasma level of cromolyn from about 10 ng/ml to about 60 ng/ml during a dosage interval. In certain other embodiments, the oral dosage form provides a mean plasma level of cromolyn from about 30 ng/ml to about 60 ng/ml during a dosage interval.

In certain embodiments, the oral dosage form provides a cromolyn sodium $C_{max}$, from about 22 ng/ml to about 1700 ng/ml. In certain other embodiments, the oral dosage form provides a cromolyn sodium $C_{max}$ from about 22 to about 77 ng/mL. In certain other embodiments, the oral dosage form provides a cromolyn sodium $C_{max}$ from about 40 to about 65 ng/mL.

In certain embodiments, the oral dosage form provides a cromolyn sodium $C_{max}$, from about 22 to about 77 ng/mL within about 0.2 to about 1 hour after oral administration.

In certain embodiments, the invention provides for the use of cromolyn sodium in the manufacture of a medicament for the oral treatment of inflammatory diseases caused or exacerbated by the release of histamine and/or cytokines from mast cells. In certain other embodiments, the invention provides cromolyn sodium for use in oral therapy for treatment of inflammatory diseases caused or exacerbated by the release of histamine and/or cytokines from mast cells.

In certain other embodiments, the invention provides for the use of cromolyn sodium in the manufacture of a medicament comprising cromolyn sodium and a delivery agent, said delivery agent comprising Sodium N-[8-(2-hydroxybenzoyl) amino]caprylate (SNAC), in ratios from about 1:30 to about 3:4 (weight/weight), for the oral treatment of inflammatory diseases caused or exacerbated by the release of histamine and/or cytokines from mast cells.

In certain embodiments, the invention provides a method for treating inflammatory diseases caused or exacerbated by the release of histamine and/or cytokines from mast cells, comprising orally administering cromolyn sodium in an amount from about 40 mg to about 1 g together with a delivery agent in an amount from about 100 mg to about 2500 mg or in a ratio from about 1:30 (weight/weight) to about 3:4 (weight/weight).

In certain embodiments, the invention provides a method for treating allergic rhinitis, asthma, rheumatoid arthritis, or autoimmune diseases caused or exacerbated by the release of histamine and/or cytokines from mast cells, comprising orally administering a therapeutically effective amount of cromolyn sodium together with a delivery agent in a ratio from about 1:30 (mg/mg) to about 3:4 (weight/weight) on a prophylactic basis.

In certain other embodiments, the invention provides a method for treating allergic rhinitis, asthma, rheumatoid arthritis, or autoimmune diseases caused or exacerbated by the release of histamine and/or cytokines from mast cells, wherein the dose of cromolyn sodium and drug delivery agent is selected from the group consisting of about 40 mg cromolyn sodium/about 1200 mg delivery agent, about 80 mg cromolyn sodium/about 1200 mg delivery agent, about 80 mg cromolyn sodium/about 600 mg delivery agent, about 80 mg cromolyn sodium/about 1200 mg delivery agent, about 120 mg cromolyn sodium/about 200 mg delivery agent, about 120 mg cromolyn sodium/about 400 mg delivery, 120 mg cromolyn sodium/about 500 mg delivery agent and about 150 mg cromolyn sodium/about 200 mg delivery agent.

In certain embodiments, the invention provides a method for treating allergic rhinitis, asthma, rheumatoid arthritis, or autoimmune diseases caused or exacerbated by the release of histamine and/or cytokines from mast cells, wherein the $T_{max}$ for cromolyn sodium occurs at a time less than about 1 hour after oral administration. In certain other embodiments, the $T_{max}$ for cromolyn sodium occurs at about 0.1 to about 1.5 hours after oral administration. In certain other embodiments, the $T_{max}$ for cromolyn sodium occurs at about 0.2 to about 0.5 hours after oral administration.

In certain embodiments, the invention provides a method for treating allergic rhinitis, asthma, rheumatoid arthritis, or autoimmune diseases caused or exacerbated by the release of histamine and/or cytokines from mast cells, wherein an AUC for cromolyn sodium of between about 16 and about 400 ng·h/mL is attained. In certain other embodiments, the invention provides a method for treating allergic rhinitis, asthma, rheumatoid arthritis, or autoimmune diseases caused or exacerbated by the release of histamine and/or cytokines from mast cells, wherein an AUC for cromolyn sodium of between about 25 and about 40 ng·h/mL is attained. In certain other embodiments, the invention provides a method for treating allergic rhinitis, asthma, rheumatoid arthritis, or autoimmune diseases caused or exacerbated by the release of histamine and/or cytokines from mast cells, wherein an AUC for cromolyn sodium of between about 30 and about 35 ng·h/mL is attained.

In certain embodiments, the invention provides a method for treating allergic rhinitis, asthma, rheumatoid arthritis, or autoimmune diseases caused or exacerbated by the release of histamine and/or cytokines from mast cells, wherein a cromolyn sodium $C_{max}$ that is from about 20 to about 250 ng/mL is attained. In certain other embodiments, the invention provides a method for treating allergic rhinitis, asthma, rheumatoid arthritis, or autoimmune diseases caused or exacerbated by the release of histamine and/or cytokines from mast cells, wherein a cromolyn sodium $C_{max}$ that is from about 22 to about 77 ng/mL is attained. In certain other embodiments, the invention provides a method for treating allergic rhinitis, asthma, rheumatoid arthritis, or autoimmune diseases caused or exacerbated by the release of histamine and/or cytokines from mast cells, wherein a cromolyn sodium $C_{max}$ that is from about 40 to about 65 ng/mL is attained.

In certain embodiments, the invention provides a method for treating allergic rhinitis, asthma, rheumatoid arthritis, or autoimmune diseases caused or exacerbated by the release of histamine and/or cytokines from mast cells, wherein a cromolyn sodium $C_{max}$ that is from about 22.3 to about 76.7 ng/mL within about 0.2 to about 1 hour after oral administration is attained.

In certain embodiments, the invention provides a method for treating allergic rhinitis, asthma, rheumatoid arthritis, or autoimmune diseases caused or exacerbated by the release of histamine and/or cytokines from mast cells, wherein cromolyn sodium and an acylated amino acid delivery agent are sequentially administered.

In certain embodiments, the invention provides an oral dosage form comprising cromolyn sodium and a pharmaceutically acceptable absorption enhancing delivery agent in an effective amount to provide therapeutically effective blood plasma levels of cromolyn upon oral administration, said dosage form providing a $T_{max}$ of cromolyn at from about 0.2 to about 0.5 hours after oral administration.

In certain embodiments, the invention provides an oral dosage form comprising cromolyn sodium and a pharmaceutically acceptable bioavailability enhancing delivery agent in an effective amount to provide therapeutically effective blood plasma levels of cromolyn upon oral administration, said dosage form providing a $C_{max}$ of cromolyn from about 4 ng/ml to about 250 ng/ml. In certain other embodiments, the delivery agent is included in said dosage form in an amount from about 200 to about 800 mg. In certain other embodiments, the delivery agent is included in said dosage form in an amount of about 500 mg to about 700 mg.

In certain embodiments, the invention provides a method of providing a therapeutically effective orally administrable dose of cromolyn sodium, comprising combining from about 40 mg to about 1 g of unmodified cromolyn with from about 100 mg to about 2500 mg of a pharmaceutically acceptable delivery agent which facilitates absorption of said cromolyn from the gastrointestinal tract of human patients, and orally administering said unit dose to a human patient to provide a therapeutic effect.

In certain embodiments, the invention provides a method of treating asthma, allergic rhinitis, autoimmune diseases and rheumatoid arthritis comprising: orally administering to a patient in need of treatment a dosage form comprising a dose of cromolyn sodium together with a delivery agent which facilitates the absorption of the cromolyn sodium from the gastrointestinal tract to provide a therapeutically effective systemic dose of cromolyn sodium.

BRIEF DESCRIPTION OF THE DRAWINGS

FIG. 1 depicts the percent airway resistance after ascaris challenge in sheep given oral cromolyn or control compositions 15 minutes prior to ascaris challenge;

FIG. 2 depicts the percent airway resistance after ascaris challenge in sheep given oral cromolyn or control compositions 60 minutes prior to ascaris challenge;

FIG. 3 depicts the percent airway resistance after ascaris challenge in sheep given oral cromolyn or control compositions 12 hours prior to ascaris challenge;

FIG. 4 depicts the plasma levels attained over time of cromolyn for individual patients given treatment period 1 in Example 4;

FIG. 5 depicts the plasma levels of cromolyn for individual patients given treatment period 2 in Example 4;

FIG. 6 depicts the plasma levels of cromolyn for individual patients given treatment period 3 in Example 4;

FIG. 7 depicts the plasma levels of cromolyn for individual patients given treatment period 4 in Example 4;

DETAILED DESCRIPTION

Figure 8:
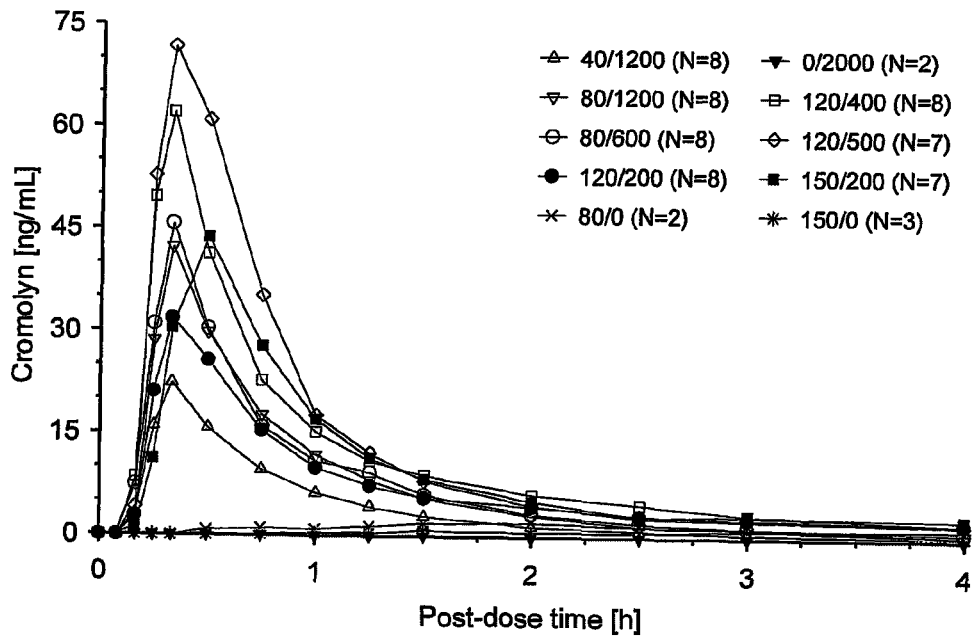
FIG. 8 depicts plasma cromolyn concentrations vs. time profiles after single oral administration of different combinations of cromolyn sodium and SNAC dosages.

The specific compositions of the present invention include an active agent and a modified amino acid. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Active agents suitable for use in the present invention include biologically active agents and chemically active agents, including, but not limited to pharmacological agents and therapeutic agents, particularly polar organic compounds and particularly compounds which by themselves do not pass (or which pass only a fraction of the administered dose) through the gastro-intestinal mucosa and/or are susceptible to chemical cleavage by acids and enzymes in the gastro-intestinal tract and are rendered less active or inactive; or any combination thereof.

In a preferred embodiment of the present invention, pharmaceutical compositions comprising cromolyn and a delivery agent molecule are provided. The term "cromolyn" is defined for purposes of the present invention as any pharmaceutically acceptable form of the drug. Pharmaceutical compositions containing cromolyn sodium, an antiallergic, are useful for mammals suffering from respiratory afflictions, such as asthma, hay fever or allergies.

Cromolyn is a synthetic compound, and it is commercially available, originally produced in the search for an improved bronchodilator. Although cromolyn has no bronchodilator activity, it was found to inhibit antigen-induced bronchospasm. Currently, its major use is as a prophylactic agent in the treatment of mild to moderate asthma. It also is used as a nasal inhaler to treat seasonal allergic rhinitis, as an ophthalmic solution to treat allergic or vernal conjunctivitis, and orally to treat systemic mastocytosis and ulcerative colitis. The chemical structure for cromolyn sodium is as follows:

Cromolyn Sodium
$C_{23}H_{14}Na_2O_{11}$

Cromolyn, or 5,5'-[(2-hydroxy-1,3-propanediyl)bis-(oxy)]4-oxo-4H-1-benzopyran-2-carboxylic acid has a molecular weight of 468.38 with the empirical formula of $C_{23}H_{16}O_{11}$. Cromolyn is also known as cromolyn sodium or disodium chromoglycate, has a melting point of 241-241° C. and is freely soluble in water. See Merck Index, Eleventh Edition, compound number 2594, page 406, the text of which is hereby incorporated by reference.

Modified Amino Acid Delivery Agent Compounds

The present invention provides compounds and compositions that are useful in the oral delivery of therapeutic compounds. Further, the present invention utilizes compounds having the following formula, or salts thereof, or mixtures thereof in the granulation and encapsulation of cromolyn. Such formulations serve to make cromolyn bioavailable and bioactive when orally administered.

In certain embodiments, the delivery agent compound has the formula and salts thereof:

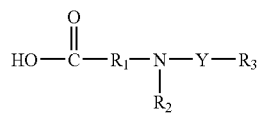

wherein Y is carbonyl (CO) or $SO_2$; $R_1$ is $C_3$-$C_{24}$ alkyl, $C_2$-$C_{20}$ alkenyl, $C_2$-$C_{20}$ alkyne, cycloalkyl, or aromatic; $R_2$ is hydrogen, $C_1$-$C_4$ alkyl, or $C_2$-$C_4$ alkenyl; and $R_3$ is $C_1$-$C_7$ alkyl, $C_3$-$C_{10}$ cycloalkyl, aryl, thienyl, pyrrolo, or pyridyl, where $R_3$ is optionally substituted by one or more $C_1$-$C_5$ alkyl group, $C_2$-$C_4$ alkenyl group, F, Cl, OH, $SO_2$, COOH, or $SO_3H$.

In a preferred embodiment, $R_1$ is $C_3$-$C_{12}$ alkyl, more preferably $C_3$-$C_9$ alkyl, more preferably $C_5$-$C_7$ alkyl, more preferably $C_7$ alkyl.

In a preferred embodiment, Y is carbonyl (CO).

In certain preferred embodiments, the delivery agent compound has the formula and salts thereof:

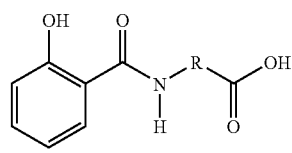

wherein R is $C_3$-$C_{24}$ alkyl, $C_2$-$C_{20}$ alkenyl, $C_2$-$C_{20}$ alkyne, cycloalkyl, or aromatic.

In certain preferred embodiments of the invention, the delivery agent is Sodium N-[8-(2-hydroxybenzoyl)amino] caprylate (SNAC) or salts thereof. These compounds, and methods of preparation of the same, are described in U.S. Pat. No. 5,650,386 (Leone-Bay, et. al.), which is hereby incorporated by reference in its entirety.

The terms modified amino acid, modified poly amino acid and modified peptide are meant to include amino acids that have been modified, or poly amino acids and peptides in which at least one amino acid has been modified, by acylating or sulfonating at least one free amine group with an acylating or sulfonating agent which reacts with at least one of the free amine groups present.

Amino acids, poly amino acids and peptides, in modified form, may be used to deliver active agents including, but not limited to, biologically or chemically active agents such as, for example, pharmacological and therapeutic agents. An amino acid is any carboxylic acid having at least one free amine group and includes naturally occurring and synthetic amino acids.

Poly amino acids are either peptides or two or more amino acids linked by a bond formed by other groups which can be linked, e.g., an ester, anhydride or an anhydride linkage. Peptides are two or more amino acids joined by a peptide bond. Peptides can vary in length from dipeptides with two amino acids to poly peptides with several hundred amino acids. See Chambers Biological Dictionary, editor Peter M. B. Walker, Cambridge, England: Chambers Cambridge, 1989, page 215. Special mention is made of di-peptides, tri-peptides, tetra-peptides and penta-peptides. Modified amino acids are typically prepared by modifying the amino acid or an ester thereof.

Many of these compounds may be prepared, e.g., by acylation or sulfonation with agents having the formula

X—Y—R$^4$ wherein R$^4$ is the appropriate radical to yield the modification indicated in the final product, Y is a carbonyl (CO) or SO$_2$, and X is a leaving group. Typical leaving groups include, but are not limited to, halogens such as, for example, chlorine, bromine and iodine. Additionally, the corresponding anhydrides are modifying agents.

Many other compounds suitable for the present invention can be readily prepared from amino acids by methods within the skill of those in the art based upon the disclosure of U.S. Pat. No. 5,650,386 to A. Leone-Bay et al., the disclosure of which is hereby incorporated by reference in its entirety. For example, compounds derived from aminobutyric acid and compounds derived from aminocaproic acid may be suitable for the present invention. For example, the modified amino acid compounds above may be prepared by reacting the single amino acid with the appropriate modifying agent which reacts with free amino moiety present in the amino acids to form amides. Protecting groups may be used to avoid unwanted side reactions, as would be known to those skilled in the art.

The amino acid can be dissolved in aqueous alkaline solution of a metal hydroxide, e.g., sodium or potassium hydroxide, and heated at a temperature ranging between about 5 EC and about 70 EC, preferably between about 10 EC and about 40 EC, for a period ranging between about 1 hour and about 4 hours, preferably about 2.5 hours. The amount of alkali employed per equivalent of NH$_2$ groups in the amino acid generally ranges between about 1.25 and about 3 mmole, preferably between about 1.5 and about 2.25 mmole per equivalent of NH$_2$. The pH of the solution generally ranges between about 8 and about 13, preferably ranging between about 10 and about 12.

Thereafter, the appropriate amino modifying agent can be added to the amino acid solution while stirring. The temperature of the mixture may be maintained at a temperature generally ranging between about 5 EC and about 70 EC, preferably between about 10 EC and about 40 EC, for a period ranging between about 1 and about 4 hours. The amount of amino modifying agent employed in relation to the quantity of amino acid is based on the moles of total free NH$_2$ in the amino acid. In general, the amino modifying agent is employed in an amount ranging between about 0.5 and about 2.5 mole equivalents, preferably between about 0.75 and about 1.25 equivalents, per molar equivalent of total NH$_2$ group in the amino acid.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between about 9 and about 13, preferably between about 11 and about 13. Insoluble materials are removed by filtration and the filtrate is dried in vacuo. The yield of modified amino acid generally ranges between about 30 and about 60%, and usually about 45%.

If desired, amino acid esters, such as, for example, benzyl, methyl or ethyl esters of amino acid compounds, may be used to prepare the modified amino acids of the invention. The amino acid ester, dissolved in a suitable organic solvent, such as dimethylformamide, pyridine or tetrahydrofuran, is reacted with the appropriate amino modifying agent at a temperature ranging between about 5 EC and about 70 EC, preferably about 25 EC, for a period ranging between about 7 and about 24 hours. The amount of amino modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the modified amino acid ester with a suitable alkaline solution, e.g., 1N sodium hydroxide, at a temperature ranging between about 50 EC and about 80 EC, preferably about 70 EC, for a period of time sufficient to hydrolyze off the ester group and form the modified amino acid having a free carboxyl group. The hydrolysis mixture is then cooled to room temperature and acidified, e.g., aqueous 25% hydrochloric acid solution, to a pH ranging between about 2 and about 2.5. The modified amino acid precipitates out of solution and is recovered by conventional means such as filtration or decantation. Benzyl esters may be removed by hydrogenation in an organic solvent using a transition metal catalyst.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0-500 mM sodium chloride gradient is employed.

In certain preferred embodiments, the delivery agent compound is Sodium N-[8-(2-hydroxybenzoyl)amino]caprylate (SNAC), having the chemical structure:

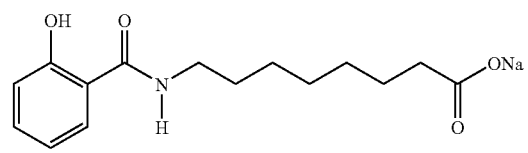

This delivery agent, SNAC, may be synthesized by methods known in the art, such as described in Examples 1, and 8-11 in International Publication Number WO 00/46182 by Gschneidner et al., (2000), which is hereby incorporated by reference.

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

In certain embodiments of the invention, the oral dosage form described herein provides a mean plasma level of cromolyn from about 4 ng/ml to about 250 ng/ml during a dosage interval. In other embodiments, the oral dosage form provides a mean plasma level of cromolyn from about 10 ng/ml to about 200 ng/ml during a dosage interval. In yet other embodiments, the oral dosage form provides a mean plasma level of cromolyn from about 30 ng/ml to about 70 ng/ml during a dosage interval. In yet other embodiments, the oral dosage form provides a mean plasma level of cromolyn from about 40 ng/ml to about 60 ng/ml during a dosage interval.

The delivery agent may be used directly by simply mixing one or more such agents with the active agent prior to administration. The delivery agent and active agent may be mixed in dry powder form or wet granulated together. Other pharmaceutically acceptable excipients may be added to this mixture. The mixture may then be tableted or placed into capsules containing a unit dose of the active agent and the delivery agent. Alternatively, the delivery agent/active agent mixture may be prepared as an oral solution or suspension. The delivery agent and active agent need not be mixed together prior to administration. In other words, in certain embodiments, the unit dose of active agent (with or without other pharmaceutically acceptable excipients) is orally administered without the delivery agents of this invention, and the delivery agent is separately orally administered (with or without other pharmaceutically acceptable excipients) before, after or simultaneously with the active agent. In yet another alternative embodiment, the delivery agent may be used to form microspheres containing the active agent.

The administration mixtures may be prepared, e.g., by mixing an aqueous solution of the delivery agent with an aqueous solution of the active ingredient, just prior to administration. Alternatively, the delivery agent and the biologically or chemically active ingredient can be admixed during the manufacturing process. The solutions may optionally contain additives such as phosphate buffer salts, citric acid, acetic acid, gelatin and gum acacia.

Stabilizing additives may be incorporated into the delivery agent solution. With some drugs, the presence of such additives promotes the stability and dispersibility of the agent in solution. The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent, e.g., cromolyn sodium, is an amount effective to accomplish the purpose of the particular active agent. The amount in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

The total amount of active agent, and particularly cromolyn sodium, to be used can be determined by those skilled in the art. However, it has surprisingly been found that with some biologically or chemically active agents, the use of the presently disclosed delivery agents provides extremely efficient delivery.

The amount of delivery agent in the present composition is a delivery effective amount and can be determined for any particular delivery agent/active agent combination by methods known to those skilled in the art.

The oral dosage forms of the present invention, containing a mixture of the active agent, e.g., cromolyn sodium, and the delivery agent, e.g., SNAC, or separately containing the active agent and the delivery agent, may include additional materials known to those skilled in the art as pharmaceutical excipients. Any excipient or ingredient, including pharmaceutical ingredients or excipients. Such pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoromethane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide);

Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Table disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients that may be used in oral dosage forms of the present invention.

Clinical Applications

In preferred embodiments in which the active agent is cromolyn sodium, the pivotal roles mast cell degranulation and release of mediators play in the genesis of allergic reactions, and the potential role of cromolyn of modifying the immune response at the top of the inflammatory cascade, are the rationale to utilize this drug in an oral form. The conditions for which cromolyn is most suited are mild to moderate asthma and allergic rhinitis.

Asthma is a serious, chronic and potentially life-threatening condition affecting an estimated 14 to 15 million people in the United States. More than 5000 people die of asthma annually, and almost all of these deaths are preventable. Prevalence rates have increased 29% in the last decade, hospitalizations by 300% and asthma death rates by 31%. Asthma causes more than 100 million days annually of restricted activity due to symptoms and 7 million outpatient visits per year for asthma-related symptoms. The costs of asthma care are enormous, approaching $6 billion per year.

Allergic rhinitis is the fifth most common chronic illness in the U.S. and, according to the Joint Task Force on the Diagnosis and Treatment of Rhinitis, allergic rhinitis affects 20 to 40 million people in the U.S. annually, including 10% to 30% of adults and up to 40% of children. The disease occurs either during the seasons of airborne pollens and molds or throughout the year, triggered by indoor allergens such as dust mites, house pets, cockroaches and molds. Allergic rhinitis usually starts in childhood, on average at about the age of 10 years. Like that of asthma, its prevalence is rising, especially in urban areas, for obscure reasons. The severity of allergic rhinitis ranges from mild to seriously debilitating and has a large impact on the quality of life of affected patients. Although many assume that allergic rhinitis is more of a nuisance than a clinically significant health problem, it is responsible for $6 billion annually in health care costs in the United States, and it frequently causes absence or poor performance at work and school.

Allergic rhinitis and asthma are atopic diseases implying IgE-mediated diseases. Individuals with atopy have a hereditary predisposition to produce IgE antibodies against common environmental allergens and often have one or more atopic diseases. On inhaling aeroallergens derived from pollen, house-dust mites, and cat dander the individual without atopy will mount a low-grade immunologic response; they produce allergen-specific IgG1 and IgG4 antibodies, and in vitro their T cells respond to the allergen with a moderate degree of proliferation and the production of interferon-by type 1 helper T (Th1) cells. Persons with atopy, by contrast, have an exaggerated response characterized by the production of allergen-specific IgE antibodies; they have elevated serum levels of IgE antibodies and positive reactions to extracts of common aeroallergens on skin-prick tests. T cells from their blood respond to allergens in vitro by inducing cytokines produced by type 2 helper T (Th2) cells (i.e., interleukin-4, 5, and 13), rather than cytokines produced by Th1 cells (interferon- and interleukin-2). The immunopathological hallmark of allergic disease is the infiltration of affected tissue by Th2 cells.

The development of specific allergic diseases may be related to alterations in the target organ. For example, the cofactors required for an asthma attack may include respiratory virus infections and exposure to allergens, tobacco smoke and air pollutants. These factors, alone or in combination, may alter immunoregulatory mechanisms at mucosal surfaces in ways that promote a Th2-mediated allergic inflammatory response. Acute allergic reactions result from the release of preformed granule-associated mediators, membrane-derived lipids, cytokines and chemokines when an allergen interacts with IgE that is bound to mast cells or basophils by the chain of the high-affinity IgE receptor.

The most important inducers of the production of IgE are interleukin-4 and interleukin-13. These cytokines initiate transcription of the gene for the epsilon class of the constant region (C) of the immunoglobulin heavy chain. The production of IgE also requires two transcription factors, nuclear factor B and STAT-6; the former pathway involves the costimulatory molecules CD40 and the CD40 ligand (CD 154), and the latter is activated when interleukin-4 binds to the high-affinitychain of the interleukin-4 receptor.

In a person with atopy, exposure of the airway to a single dose of allergen produces an immediate hypersensitivity reaction manifesting itself as sneezing and runny nose, or wheezing within minutes. Depending on the amount of the allergen, these immediate hypersensitivity reactions are followed by a late-phase reaction, which reaches a peak six to nine hours after exposure to the allergen and then slowly resolves.

Immediate hypersensitivity is the basis of acute allergic reactions. It is caused by molecules released by mast cells when an allergen interacts with membrane-bound IgE. The complex of allergen, IgE and Fc RI on the surface of the mast cell triggers a noncytotoxic, energy-dependent release of preformed, granule-associated histamine and tryptase and the membrane-derived lipid mediators leukotrienes, prostaglandins, and platelet-activating factor. (Tryptase is a four-chain neutral protease that activates the protease-activated receptors on endothelial and epithelial cells). The leukotriens produced by mast cells are the three cysteinyl leukotrienes $C_4$, $D_4$ and $E_4$, which cause the contraction of smooth muscles, vasodilatation, increased vascular permeability and the hypersecretion of mucus when they bind to specific receptors. The activation of the specific receptors initiates a cascade of events, including the up-regulation of adhesion molecules that selectively attract eosinophils and basophils. The mast-cell mediators have a critical role in anaphylaxis, rhinoconjunctivitis and urticaria.

In the late-phase asthmatic and nasal reaction, eosinophils and neutrophils accumulate, and then CD4+ T cells (in the cutaneous late phase response also basophils infiltrate the site). Depending on the target organ, late-phase reactions can be provoked by the activation of mast cells or T cells. Late-phase reactions can be induced in patients with atopic asthma in the absence of immediate hypersensitivity involving mast cells.

Pharmacokinetics:

Systemic bioavailability of oral cromolyn (administered without the delivery agents of the present invention) is approximately 1%. Nevertheless, cromolyn is administered orally to treat systemic mastocytosis and inflammatory bowel disease. Minimal systemic absorption occurs after either intranasal or ophthalmic use. Roughly 5-10% of an inhaled dose reaches the lungs. The amount reaching the lungs after inhalation is affected by the degree of bronchoconstriction present. Cromolyn does not traverse cell membrane walls well because it is highly lipid-insoluble and mainly ionized. Several weeks of therapy may be required before improvement is apparent. Little of the drug crosses the placenta or distributes into breast milk. Roughly 98% of the dose is eliminated unchanged in the feces.

Mechanism of Action:

Mucosal inflammation is characterized by early and late phases. The early phase results from IgE-mediated mast cell degranulation. Cromolyn works at the surface of the mast cell to inhibit its degranulation. This, in turn, prevents the release of histamine and slow-reacting substance of anaphylaxis (SRS-A), mediators of type I allergic reactions. Cromolyn also may reduce the release of inflammatory leukotrienes. It has been postulated that cromolyn produces these effects by inhibiting calcium influx, but its exact mechanism of action is unclear. Cromolyn does not interfere with the binding of IgE to the mast cell or with the binding of antigen to IgE. Because cromolyn is not a bronchodilator, an antihistamine or a vasoconstrictor, its beneficial effects in the treatment of asthma are largely prophylactic. Cromolyn can reduce hyperreactivity of the bronchi, inhibiting asthmatic responses to antigenic challenge (e.g., cold air, allergens, environmental pollutants) or to exercise.

The late phase bronchospastic response of asthma is characterized by interstitial edema, mucous glycoprotein release, and eosinophil infiltration of the airways. Leukotrienes attract cellular infiltrates producing epithelial injury, abnormalities in neural mechanisms, increases in airway smooth muscle responsiveness and airway obstruction. Cromolyn may reduce the release of inflammatory leukotrienes. It has been postulated that cromolyn produces these effects by inhibiting calcium influx, but its exact mechanism of action is unclear. An exaggerated bronchoconstrictor response, airway hyperresponsiveness, can be induced by a variety of causes including cold air, allergens, environmental pollutants or exercise. Cromolyn can reduce hyperreactivity of the bronchi, inhibiting asthmatic responses to antigenic challenge.

The guidelines for the diagnosis and management of asthma depend on the severity of the disease and patient age, factors which determine which therapy to initiate. Both adults and children with chronic mild asthma can effectively prevent asthma attacks with cromolyn. Cromolyn is first line therapy for prophylaxis because it is well tolerated, displaying only minor adverse reactions. For the chronic treatment of moderate asthma, cromolyn continues to be the respiratory antiinflammatory agent of choice, with inhaled or oral corticosteroids as an acceptable option.

As the severity of the disease progresses, therapy becomes more intense. Inhaled corticosteroids are first line agents for both adults and children, with or without cromolyn or other agents. If not effectively controlling symptoms, short burst of oral corticosteroids or chronic alternate day therapy should be considered. If symptoms are severe enough in children, systemic corticosteroid therapy may be considered; risk-benefit should be weighed in this therapeutic decision. The use of intravenous corticosteroids is limited to the treatment of acute exacerbations of asthma in patients in the emergency room or in hospitalized patients.

As discussed above, cromolyn sodium inhibits antigen-triggered release of mediators from sensitized mast cells. Cromolyn sodium stabilizes the mast cell membrane and is believed to function in part by being bound to the mast cell membranes.

In contrast to previously available low dosages of cromolyn sodium (i.e., Gastrocrom®), which is available in 100 mg ampoules and which upon oral administration of which no more than 1% of the administered dose is absorbed, the oral formulations of the present invention provide a greatly enhanced oral absorption of cromolyn sodium and can achieve this increased absorption at a more rapid rate. For this reason, the oral doses of cromolyn sodium plus delivery agent as described herein are contemplated for use in a wide range of disease states which may be mediated or exacerbated by a proliferation or infiltration of mast cells and degranulation of these mast cells, thereby causing an inflammatory condition. Plus, it is contemplated that the formulations of the present invention maybe used as anti-inflammatory formulations to prevent the release of leveators from sensitized mast cells. Inflammatory conditions contemplated for treatment by the formulations of the present invention include any systemic inflammatory condition known to those skilled in the art, including but not limited to autoimmune diseases, rheumatoid arthritis, and cardiovascular disease. Many other disease states which are caused by or exacerbated by inflammatory conditions caused by the release of mediators from sensitized mast cells may also be treated utilizing the oral formulations of the present invention.

By virtue of the fact that the oral dosage forms of the present invention provide an increased absorption of cromolyn sodium as compared to any other treatments to date, the cromolyn sodium may be delivered to the systemic circulation of the effected patients in a higher level than previously possible. In view of the fact that cromolyn sodium binds to mast cells and functions in this manner, the duration of action of the cromolyn sodium may be dependent upon the amount absorbed. Therefore, it is contemplated that the oral dosage forms of the present invention provide a longer acting product, and may be administrable at greater intervals (i.e. once a day) and still achieve the desired therapeutic effect.

Furthermore, it is contemplated that, in contrast to generally accepted treatment regimens, the systemic administration of cromolyn sodium may be more efficacious in certain disease states to treat a localized inflammatory condition (e.g., asthma) than a localized treatment of cromolyn sodium form asthma (e.g., via a metered dose inhaler (MDI)). This is because, in disease states such as asthma, the most diseased airways are restricted to the greatest extent and therefore have the least airflow, while the least diseased airways have the greatest airflow. Therefore, local administration of cromolyn sodium via MDI will likely result in the greatest amount of drug flowing to the areas that least require treatment. In contrast, via the systemic administration of cromolyn sodium via the oral formulations of the present invention, the localized area (e.g., lungs) can be treated equally across the entire area, thereby insuring that sufficient levels of cromolyn sodium reach the most restricted passage ways of the lung.

In further embodiments of the present invention, it is contemplated that the oral dosage forms of the invention may be used to treat any inflammatory condition wherein inflammatory process is related at least in part to the release of cytokines or histamine from mast cells.

It is further contemplated that the oral dosage forms of the present invention may be used to treat alert allergies, including but not limited to allergic rhinitis. For seasonal allergies, it is contemplated that the oral dosage forms of the present invention are administered on a regular basis beginning early in the season and are continued prophylactically throughout the allergy season. For very severe allergies, it is contemplated that the administration of the oral dosage forms of the present invention may occur on a once-every-four-hours basis. However, it is contemplated that the oral dosage forms of the invention can be administered for treatment of allergy on a once-a-day basis in many situations, as well.

It is further contemplated that the oral dosage of the present invention can be utilized for the treatment of allergic conjunctivitis. In such embodiments, it is contemplated that a sufficient plasma concentration of cromolyn sodium is obtained via the oral administration to reach the affected area and provide an effective treatment.

In certain preferred embodiments, the oral formulations of the present invention include cromolyn sodium in unmodified form in an amount form about 40 mg to about 1 g, and more preferably in an amount from about 80 mg to 100 mg, together with a drug delivery agent (e.g. SNAC) in an amount from about 200 mg to about 2500 mg.

As demonstrated by the appended examples, the oral dosage forms of the present invention in certain preferred embodiments provide a rapid absorption of cromolyn sodium systemically in a significantly greater percentage than previously reported. In certain preferred embodiments, this rapid absorption is characterized by the time to maximum plasma concentration $T_{max}$ within about 1 hour after oral administration of the dosage form, and in certain embodiments occurring at a time point at from about 0.2 to about 0.5 hours after oral administration of the oral dosage forms of the present invention.

The oral dosage forms of the present invention containing cromolyn sodium plus the delivery agent are described by virtue of the $C_{max}$ and AUC of the cromolyn sodium following oral administration of the dose. Although these pharmacokinetic parameters are characteristic of certain embodiments of the oral dosage forms of the present invention, it will be appreciated by those skilled in the art that the measured plasma concentration of cromolyn sodium may not be directly tied to efficacy of or activity of the oral dosage form, as there have been no studies reported to date concerning the absolute relationship in humans between plasma level and activity or disease states contemplated treatment in the present invention.

Due to the greater levels of systemic absorption afforded to cromolyn sodium by the oral dosage forms of the present invention, it is contemplated that the duration of action may be dependent on the total amount of drug absorbed from the gastrointestinal tract. Therefore, it is contemplated that the oral dosage forms of the present invention may provide the prolonged activity of cromolyn sodium in comparison to other cromolyn sodium treatments used to date. However, it is also contemplated that, in certain circumstances, e.g., in the treatment of severe inflammatory conditions, the oral dosage forms of the present invention may be administered as often as every 4 hours to human patients. It is further contemplated that the oral dosage forms of the present invention may be administered on a less frequent basis, e.g., 4 times a day, 3 times a day, twice a day, and once a day.

In certain preferred embodiments of the present invention, the oral dosage form is a solid dosage form which contains the cromolyn sodium in an effective amount together with the drug delivery agents of the present invention in a requisite ratio to provide suitably enhanced absorptivity of the cromolyn sodium from the gastrointestinal tract upon oral administration. In embodiments of the present invention wherein a relatively large amount of cromolyn sodium is administered together with the requisite amount of drug delivery agent, or wherein a large amount of drug delivery is required to provide the requisite absorptivity, it is further contemplated that the dose may be divided into multiple capsules or tablets and administered to the patient at the same time. In this manner, even large amounts of drug/delivery agent combinations can be administered orally to the patient without patient experiences problems swallowing the dose. In yet other embodiments of the invention contemplated herein, the cromolyn sodium/drug delivery agent combination may be prepared in the form of a dry powder which is suspended in a liquid for oral administration prior to use, thereby negating the necessity of administering multiple unit doses of the dosage forms of the present invention in order to attain the desired dosage level of drug.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

DETAILED DESCRIPTION OF THE PREFERRED EMBODIMENTS

In order that this invention may be better understood, the following examples are set forth to illustrate various aspects of the present invention. These examples are for the purpose of illustration only and are not to be construed as limiting the scope of the invention or the scope of the claims in any manner.

Example 1

Male Sprague-Dawley rats weighing 225-275 grams were fasted for 24 hours. Rats were anesthized by intramuscular injection with ketamine and thorazine. Experimental groups were dosed by oral gavage or by intravenous injection. Blood samples were collected serially via the tail artery. Serum obtained from whole blood was acidified and cromolyn extracted with ethyl acetate. The ethyl acetate was added to phosphate buffer or back extraction of cromolyn. Pharmacokinetic parameters were determined from extracted serum by HPLC. For intravenous administered cromolyn (1.5 mg/kg), the area under the serum concentration-time curve (AUC), peak serum concentration ($C_{max}$) and time of peak serum concentration ($T_{max}$) were 20.4 µg-min/ml, 1.3 µg/ml and 0 minutes, respectively. When a delivery agent and cromolyn (30 mg/kg) are co-administered orally, the AUC, $C_{max}$ and $T_{max}$ were 18.3 µg-min/ml, 0.65 µg/ml and 15 minutes, respectively. No detectable serum cromolyn concentrations were observed in the control groups of delivery agent alone and cromolyn alone. An absolute oral bioavailability of 4.5% was achieved in rats. Results for the administration of cromolyn to rats are in Table 1.

TABLE 1

Administration of Cromolyn to Rats

| Delivery Agent (mg/kg) | Cromolyn (mg/kg) | Route of Administration | n | Avg. $C_{max}$ (ug/ml) | $T_{max}$ (min) | Avg. AUC (ug·min/ml) |
|---|---|---|---|---|---|---|
|  | 1.5 | IV | 5 | 1.3 | 0 | 20.4 |
|  | 30 | P.O. | 5 | 0.04 | 15 | 1.03 |
| 200 |  | P.O. | 5 | 0.10 | 30 | 9.03 |
|  | 30 | P.O. | 5 | 0.65 | 120 | 18.3 |

Example 2

Male and female Cynomolgus monkeys were fasted for 24 hours. Monkeys were gavaged with a solution of delivery agent and cromolyn. Serum obtained from whole blood was acidified and cromolyn extracted with ethyl acetate. The ethyl acetate was added to phosphate buffer for back extraction of cromolyn. Pharmacokinetic parameters were determined from extracted serum by HPLC. The AUC, $C_{max}$ and $T_{max}$ from orally dosing capsules containing the delivery agent and cromolyn (25 mg/kg) were 48.8 µg-min/ml, 0.30 µg/ml and 130 minutes, respectively.

Example 3

In order to obtain an in vivo evaluation of the oral administration of cromolyn to sheep, a preparation of delivery agent and cromolyn was prepared and administered to fasted sheep by oral gavage, 15 minutes prior to challenge with ascaris. A control formulation without cromolyn was also administered to an additional group. The biological effect of the cromolyn was assessed using changes in airway resistance of the sheep after challenge with ascaris.

In one study, the oral doses of cromolyn and delivery agent were administered 15 minutes before ascaris challenge. The results are depicted in FIG. 5, which is a graph depicting the percent airway resistance after ascaris challenge in the sheep over time. As can be seen from FIG. 5, in this study, the oral cromolyn reduced the change in airway resistance by 200%. In animals not receiving cromolyn, the change in airway resistance was plus 500% after ascaris challenge and in animals receiving cromolyn the change in airway resistance was 300%. Even given within 15 minutes of ascaris challenge the allergic symptoms were substantially alleviated.

In a second study, the oral doses of cromolyn and delivery agent were administered 60 minutes before ascaris challenge. The results are depicted in FIG. 6, which is a graph depicting the percent airway resistance after ascaris challenge in the sheep over time. As can be seen from the results depicted in FIG. 6, in this study the oral cromolyn reduced the change in airway resistance between about 350 to 400%. In animals not receiving cromolyn, the change in airway resistance was plus 440% after ascaris challenge and in animals receiving cromolyn the change in airway resistance was approximately 60%. Therefore, if the cromolyn formulations of the present invention are given about 1 hour prior to ascaris challenge the allergic symptoms were substantially eliminated.

In a third study, an oral dose of 100 mg/kg cromolyn and 300 mg/kg delivery agent were administered to fasted sheep by oral gavage, 12 hours prior to challenge with ascaris. A control formulation without cromolyn was also administered to an additional group. The biological effect of the cromolyn was assessed using changes in airway resistance of the sheep after challenge with ascaris. The results are tabulated in Table 2 below and are depicted in FIG. 8, which is a graph depicting the percent airway resistance after ascaris challenge in the sheep over time.

TABLE 2

Administration of Cromolyn to Sheep, 12 hours prior to ascaris challenge:
Compound: CR-1 & Cromolyn
Dose: 300 mg/kg CR-1 & 100 mg/kg Cromolyn given oral 12 hrs. before Ag. challenge
Ascaria Acute Study

| Sheep# | Baseline RL | P-Acaris RL | % | +1 hr. RL | % | +2 hr. RL | % |
|---|---|---|---|---|---|---|---|
| Control Trial: | | | | | | | |
| 2067 | 0.98 | 7.77 | 693% | 3.55 | 262% | 2.10 | 114% |
| 2080 | 0.94 | 7.33 | 680% | 5.10 | 442% | 3.00 | 219% |
| Means: | 0.96 | 7.55 | 687% | 4.33 | 352% | 2.55 | 167% |
| S.D.: | 0.03 | 0.31 | 9% | 1.10 | 127% | 0.64 | 74% |
| S.E.: | 0.02 | 0.22 | 6% | 0.78 | 90% | 0.45 | 53% |
| Drug Trial: | | | | | | | |
| 2067 | 0.95 | 1.64 | 73% | 1.04 | 9% | 0.97 | 2% |
| 2080 | 0.98 | 3.33 | 240% | 1.54 | 57% | 0.98 | 0% |
| Means: | 0.97 | 2.49 | 157% | 1.29 | 33% | 0.98 | 1% |
| S.D.: | 0.02 | 1.20 | 118% | 0.35 | 34% | 0.01 | 1% |
| S.E.: | 0.01 | 0.85 | 84% | 0.25 | 24% | 0.01 | 1% |

In animals not receiving cromolyn, the change in airway resistance was plus 687% after ascaris challenge and in animals receiving cromolyn the change in airway resistance was approximately 157%. The mean protection with this carrier vs. the peak control response is 77%. Therefore, if the cromolyn formulations of the present invention are given about 12 hours prior to ascaris challenge the allergic symptoms were substantially eliminated.

Example 4

Cromolyn sodium was orally administered to healthy human subjects in a study designed to evaluate the safety, tolerability, oral absorption and pharmacokinetics data following various doses of cromolyn orally administered in combination with the delivery agent SNAC as capsules. The oral administration was accomplished using capsules containing the specified dose of cromolyn sodium and sodium N-[8-(2-hydroxybenzoyl)amino]caprylate (SNAC) synthesized, e.g., as described in Examples 1 and 8-11 in International Publication Number WO 00/46182 by Gschneidner et al., (2000). This study was a randomized, open label, oral, single escalating dose administration study in healthy, fasted volunteers.

The volunteers were all males between 18 and 50 years of age, in good health, with a body weight resulting in a Body Mass Index (BMI) between 18.0 and 28.0 kg/m$^2$ inclusive, calculated as the body mass/(Height)$^2$. All laboratory values (electrocardiogram, hematology, serum chemistries, and urinalysis) obtained during screening were within normal ranges.

The study was carried out in two parts. In the first clinical part, ten subjects received four escalating single doses of Cromolyn/SNAC, and two subjects received two other treatments (80 mg of cromolyn alone as a first treatment, and 2000 mg of SNAC alone as a second treatment). The dosing regimen is indicated in Table 3 below. Eight subjects (subjects nos. 11 to 18) were included in the second clinical part, and dosed as indicated in Table 4 below. Safety and pharmacokinetic measures were collected and evaluated following each dose. If the observed cromolyn concentration was higher than the desired concentration (i.e., about 10-20 ng/ml range), the next dose was modified.

TABLE 3

Dosing regimen in subjects nos. 1-10

| Treatment Period | Cromolyn/SNAC (mg/mg) (subjects nos. 1 to 8) | Cromolyn/SNAC alone (mg/mg) (subjects nos. 9 and 10) |
|---|---|---|
| Period 1 | 40/1200 | 80/0 |
| Period 2 | 80/1200 | 0/2000 |
| Period 3 | 80/600 | ND |
| Period 4 | 120/200 | ND |

ND: no more dosing

TABLE 4

Dosing regimen in additional subjects nos. 11 to 18

| Treatment Period | Cromolyn/SNAC (mg/mg) (7 subjects) | Cromolyn/SNAC (mg/mg) (one subject) |
|---|---|---|
| Period 1 | 120/400 | 150/0 |
| Period 2 | 120/500 | 150/0 |
| Period 3 | 150/200 | 150/0 |

The initial cromolyn dose of 40 mg was selected based on preclinical studies and cromolyn therapeutic concentration levels. The clinical therapeutic concentration of cromolyn is about 0.01 μg/ml. It is stated in the Physician's Desk Reference that the therapeutic levels of cromolyn was achieved after inhalation dose of 20 mg with an cromolyn absolute bioavailability of about 8%. Preclinical study with cromolyn/SNAC in rats demonstrated that the cromolyn absolute bioavailability of about 4%. Assuming similar absolute bioavailability in rats and humans, the initial dose was selected to be 40 mg cromolyn combined with 1200 mg SNAC. The escalation of the SNAC dose from 1200 mg to 2000 mg was selected based upon the results of the nonclinical studies and a clinical safety and tolerability study.

On day one of each study treatment period, medication (capsules) was administered following an 8-hour overnight fast. The capsules were swallowed with up to 120 mL of water to the subjects in an upright position. After each dosing, safety, and pharmacokinetic measures were taken, and cromolyn concentrations were evaluated. The sponsor and the investigator together decided the administration of the next dose after reviewing safety measurements and cromolyn plasma concentration of the current dose. If the observed cromolyn concentration was higher than the therapeutic concentration (i.e., about 10-20 ng/mL range), the next dose was reduced or the current dose was repeated.

Cromolyn/SNAC capsule formulations containing varying cromolyn/SNAC ratios were prepared extemporaneously at the study site. The process could be summarized as follows: First, sieve SNAC powder through a screen, or delump it using a pestle/mortar. Then, weigh the exact dose of SNAC powder (delumped) and add to a mortar or to a suitable container, and weigh the exact dose of cromolyn and add to SNAC pre-weighed in the container. Carefully mix cromolyn/SNAC powders and fill all the powder in the capsule shells provided. For the subjects receiving cromolyn alone, the appropriate amount for cromolyn was blended with an inactive excipient, METHOCEL E15 PREMIUM LV, and packaged in four hard gelatin capsules. Each capsule contained about 2100 mg solids (SNAC and Cromolyn sodium USP). Capsules were prepared at the following dosages (mg cromolyn/mg SNAC): 0/2000, 40/1200, 80/0, 80/600, 80/1200, 120/200, 120/400, 120/500, 150/0 and 150/200.

Following administration, blood samples (5 mL in tri-sodium citrate tube) were drawn immediately before dosing (0), and at 5, 10, 15, 20, 30, and 45 minutes and 1, 1.25, 1.5, 2, 2.5, 3, 4, 6 and 8 hours postdose (16 samples per treatment) for cromolyn and SNAC measurements in all treatment groups.

The effect of oral administration of either SNAC alone or cromolyn alone in human subjects was evaluated. The average pharmacokinetic parameters derived for cromolyn in plasma after single administration of the different combination treatments of cromolyn sodium and SNAC dosages are summarized in Table 5 below.

The plasma levels of cromolyn for individual subjects given treatment number 1 are depicted in FIG. 4. The plasma levels of cromolyn for individual subjects given treatment number 2 are depicted in FIG. 5. The plasma levels of cromolyn for individual subjects given treatment number 3 are depicted in FIG. 6. The plasma levels of cromolyn for individual subjects given treatment number 4 are depicted in FIG. 7.

Figure 9:
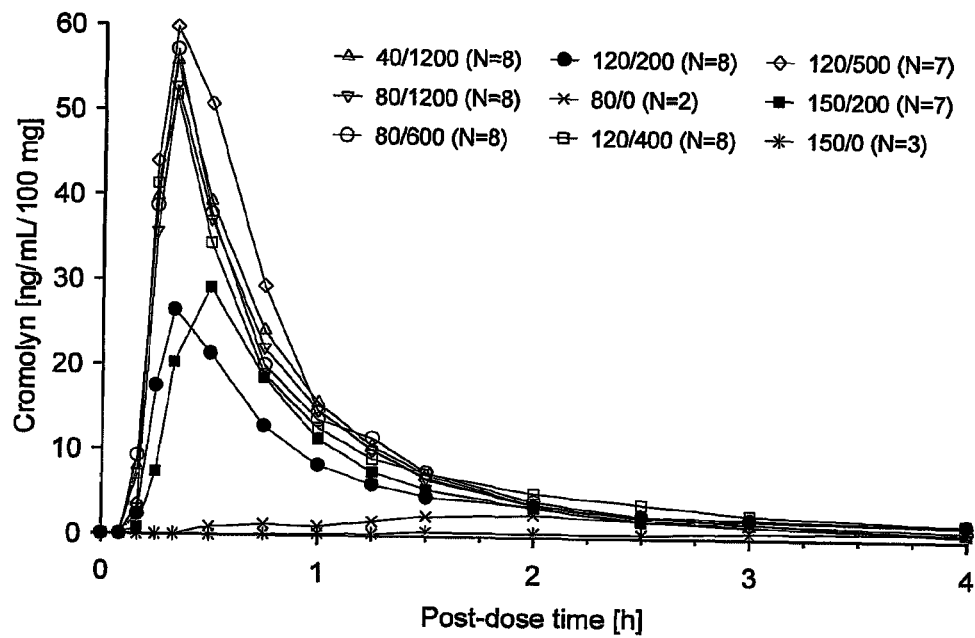
FIG. 9 depicts plasma cromolyn concentrations vs. time profiles normalized to a 100-mg dose of cromolyn sodium after single oral administration of different combinations of cromolyn sodium and SNAC dosages.

Profiles of average plasma cromolyn concentration versus time after single oral administration of different combinations of cromolyn sodium and SNAC dosages expressed as cromolyn/SNAC (mg/mg) are illustrated in FIG. 8 (original values) and FIG. 9 (after normalization to a 100 mg dose of cromolyn). In these figures, values are arithmetic means.

The cromolyn absorbed through oral administration of capsules containing SNAC and cromolyn is bioavailable and bioactive. As summarized in Table 4, cromolyn that has been granulated with SNAC and encapsulated achieves a maximal plasma level in human subjects in less than 30 minutes. As shown in Table 5, mean plasma levels ranging from about 22.3 ng/ml to about 76.7 ng/ml are achieved using this oral formulation.

No cromolyn was administered to subjects with a dosage of 2000 mg of SNAC. Regarding the peak ($C_{max}$) and extent ($AUC_{(0-t)}$) of exposure to cromolyn, the other treatments could be classified in three groups:

When patients were administered cromolyn without SNAC (i.e., 80/0 and 150/0), the plasma cromolyn concentration was very low with normalized $C_{max}$ below 3 ng/mL/100 mg and $AUC_{(0-t)}$ not exceeding 10 ng·h/mL/100 mg. The peak cromolyn concentration occurred between 2 to 8 hours after administration and plasma concentrations never reached the therapeutic level (i.e., at least 10 ng/mL). When cromolyn is administered without the delivery agent of the present invention, it is not significantly absorbed or bioavailable. See FIGS. 8 and 9.

When patients were administered cromolyn with 200 mg of SNAC (i.e., 120/200 and 150/200), the plasma cromolyn concentration increased rapidly with normalized $C_{max}$ around 30 ng/mL 100 mg and $AUC_{(0-t)}$ around 30 ng·h/mL/100 mg. In all subjects, the peak concentration was observed within 45 minutes after administration. The therapeutic cromolyn plasma level was not reached in subjects nos. 3 and 7 after administration of 120 mg of cromolyn, but was reached for at least 30 minutes in all subjects after administration of 150 mg.

When patients were administered cromolyn with higher SNAC doses (400 to 1200 mg), cromolyn absorption was still higher with normalized $C_{max}$ between 53 and 64 ng/mL/100 mg and $AUC_{(0-t)}$ between 39 and 50 ng·h/mL/100 mg. In all subjects, the peak concentration was observed within 30 minutes after administration. The therapeutic cromolyn plasma level was not reached in subject no. 7 after administration of 40 mg of cromolyn sodium combined with 1200 mg of SNAC, and in subject no. 14 administered with 120 mg of cromolyn sodium and 400 mg of SNAC. High cromolyn plasma concentrations were found in subject no. 13 after administration of 120 mg of cromolyn combined with 400 and 500 mg of SNAC ($C_{max}$ reached respectively 172 and 229 ng/mL).

The plasma levels of cromolyn achieved with these formulations were significantly higher than those seen with pulmonary delivery of cromolyn at therapeutic doses.

TABLE 5

| Cromolyn/SNAC [mg/mg] | $C_{max}$ [ng/mL] | $T_{max}$ [h] | $AUC_{(0-t)}$ [ng·h/mL] | $MRT_{(0-t)}$ [h] | $C_{max}/D^*$ [ng/mL] | $AUC_{(0-t)}/D^*$ [ng·h/mL] |
|---|---|---|---|---|---|---|
| 40/1200 (N = 8) | 22.3 ± 12.3 | 0.33-0.33 | 16.5 ± 7.9 | 1.31 ± 0.57 | 55.8 ± 30.7 | 41.2 ± 19.8 |
| 80/1200 (N = 8) | 42.3 ± 21.3 | 0.25-0.33 | 31.4 ± 15.7 | 1.22 ± 0.44 | 52.9 ± 26.6 | 39.2 ± 19.6 |
| 80/600 (N = 8) | 45.9 ± 24.7 | 0.25-0.37 | 33.4 ± 14.2 | 1.41 ± 0.23 | 57.3 ± 30.9 | 41.8 ± 17.8 |
| 120/200 (N = 8) | 33.8 ± 28.0 | 0.33-0.75 | 34.9 ± 22.4 | 2.23 ± 0.83 | 28.2 ± 23.3 | 29.1 ± 18.7 |
| 80/0 (N = 2) | 2.33 ± 0.87 | 2.00-3.00 | 7.97 ± 0.24 | 3.65 ± 0.37 | 2.91 ± 1.09 | 9.96 ± 0.30 |
| 120/400 (N = 8) | 65.5 ± 52.5 | 0.25-0.50 | 52.7 ± 37.1 | 1.94 ± 0.64 | 54.5 ± 43.7 | 43.9 ± 30.9 |
| 120/500 (N = 7) | 76.7 ± 75.5 | 0.33-0.50 | 59.7 ± 60.9 | 1.64 ± 0.40 | 64.0 ± 62.9 | 49.8 ± 50.7 |
| 150/200 (N = 7) | 51.1 ± 29.3 | 0.33-0.52 | 48.5 ± 25.1 | 2.14 ± 0.46 | 34.1 ± 19.5 | 32.3 ± 16.7 |
| 150/0 (N = 3) | 2.06 ± 0.85 | 4.00-8.00 | 8.53 ± 2.94 | 5.06 ± 0.57 | 1.37 ± 0.56 | 5.69 ± 1.96 |

*Normalized to a 100-mg dose of cromolyn sodium

Values are mean ± SD, except range for $T_{max}$.

Further evidence of the bioavailability of oral cromolyn formulated according to the present invention is demonstrated by the area under the plasma concentration-time curve (AUC) of cromolyn after oral administration. As shown in Table 5, the AUC ranged from 16.5 to 59.7 ng-hr/ml.

Figure 10:
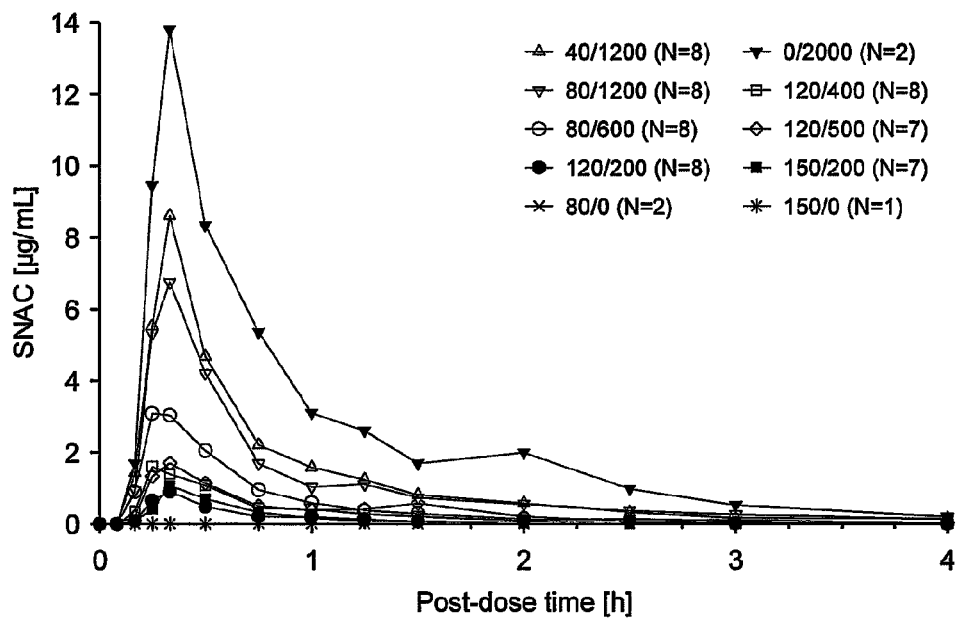
FIG. 10 depicts plasma SNAC concentrations vs. time profiles after single oral administration of different combinations of cromolyn sodium and SNAC dosages.
Figure 11:
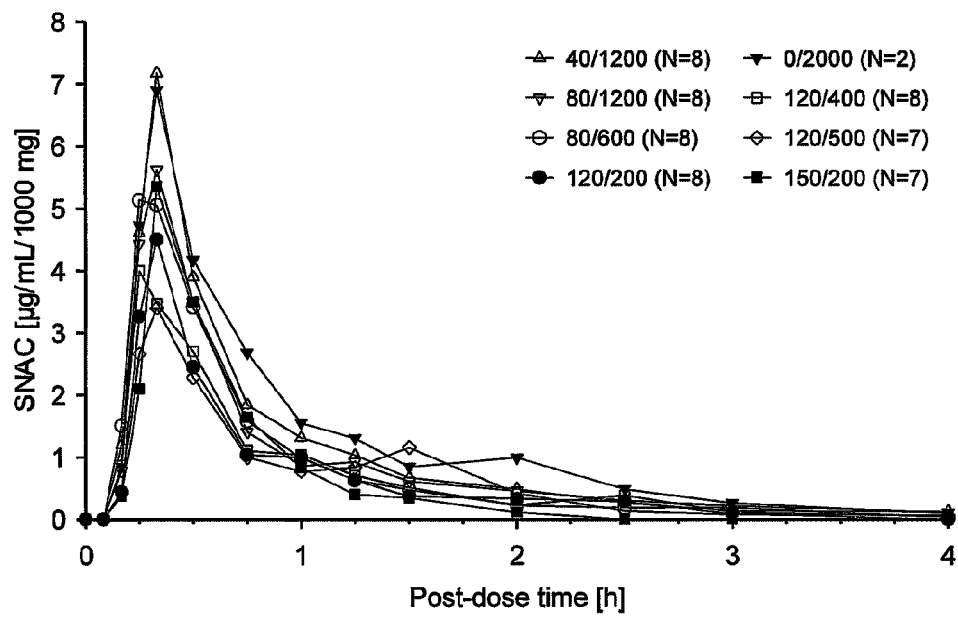
FIG. 11 depicts plasma SNAC concentrations vs. time profiles normalized to a 1000-mg dose of SNAC after single oral administration of different combinations of cromolyn sodium and SNAC dosages.

Profiles for average SNAC plasma concentration versus time after single oral administration of different combinations of cromolyn sodium and SNAC dosages expressed as cromolyn/SNAC (mg/mg) are illustrated in FIG. 10 (original values) and FIG. 11 (after normalization to a 1000 mg dose of SNAC) below.

Average pharmacokinetic parameters derived for SNAC in plasma after single oral administration of the different combinations of cromolyn sodium and SNAC dosages are summarized in Table 6 below.

TABLE 6

| Cromolyn/SNAC [mg/mg] | $C_{max}$ [µg/mL] | $T_{max}$ [h] | $AUC_{(0-t)}$ [µg·h/mL] | $MRT_{(0-t)}$ [h] | $C_{max}/D^*$ [µg/mL] | $AUC_{(0-t)}/D^*$ [µg·h/mL] |
|---|---|---|---|---|---|---|
| 40/1200 (N = 8)  | 8.64 ± 5.54  | 0.33-2.00 | 5.16 ± 1.44  | 1.26 ± 0.77 | 7.20 ± 4.62 | 4.30 ± 1.20 |
| 80/1200 (N = 8)  | 6.91 ± 2.88  | 0.25-0.50 | 4.56 ± 1.50  | 1.28 ± 0.42 | 5.76 ± 2.40 | 3.80 ± 1.25 |
| 80/600 (N = 8)   | 3.73 ± 1.59  | 0.25-0.75 | 1.98 ± 0.69  | 0.94 ± 0.23 | 6.22 ± 2.66 | 3.30 ± 1.15 |
| 120/200 (N = 8)  | 0.93 ± 0.87  | 0.25-0.33 | 0.52 ± 0.24  | 1.00 ± 0.45 | 4.65 ± 4.35 | 2.58 ± 1.18 |
| 0/2000 (N = 2)   | 13.8 ± 9.2   | 0.33-0.33 | 10.1 ± 2.9   | 1.18 ± 0.12 | 6.89 ± 4.61 | 5.05 ± 1.41 |
| 120/400 (N = 8)  | 1.86 ± 1.01  | 0.25-1.00 | 1.12 ± 0.29  | 1.07 ± 0.36 | 4.66 ± 2.53 | 2.79 ± 0.72 |
| 120/500 (N = 7)  | 2.05 ± 1.13  | 0.33-1.50 | 1.34 ± 0.45  | 1.10 ± 0.21 | 4.09 ± 2.25 | 2.67 ± 0.91 |
| 150/200 (N = 7)  | 1.25 ± 0.83  | 0.33-0.52 | 0.51 ± 0.15  | 0.72 ± 0.21 | 6.23 ± 4.13 | 2.57 ± 0.75 |

*Normalized to a 1000-mg dose of SNAC
Values are mean ± SD, except range for $T_{max}$ SNAC, when administered alone as described above, did not display any significant effect on human subjects.

No SNAC was found in control subjects administered with cromolyn only (80/0: two subjects, 150/0: one subject).

The differences observed among SNAC $C_{max}$ normalized to a 1000-mg dose of SNAC (means between 4.09 and 7.20 µg/mL) were not relevant when compared to the large observed inter-subject variability (CV between 42 and 94%). By contrast, $AUC_{(0-t)}$ normalized to a 1000-mg dose of SNAC exhibited a lower inter-subject variability (CV between 26 and 46%) and increased with the SNAC dose, in particular for SNAC dosages above 500 mg.

Due to the design of the study, high SNAC dosages (>500 mg) were associated with low doses of cromolyn (≦80 mg), whereas lower SNAC dosages were associated with at least 120 mg of cromolyn. An explorative statistical analysis showed that the increase observed for dose-normalized $AUC_{(0-t)}$ was due rather to the increase of SNAC dosages (p=0.025) than to an influence of cromolyn (p=0.11).

Pharmacokinetics

When 80 or 150 mg of cromolyn were administered without SNAC, absorption of cromolyn was very low, and plasma concentrations never reached the therapeutic level (i.e., at least 10 ng/mL). However, co-administration with SNAC enhanced the oral absorption of cromolyn. When 120 or 150 mg of cromolyn were administered in combination with 200 mg of SNAC, the dose-normalized $C_{max}$ and $AUC_{(0-t)}$ reached 30 ng/mL/100 mg and 30 ng·h/mL/100 mg, respectively.

When 40 to 120 mg of cromolyn were administered in combination with 400 to 1200 mg of SNAC, the oral absorption of cromolyn was still higher with dose-normalized $C_{max}$ and $AUC_{(0-t)}$ reaching respectively 53 64 ng/mL/100 mg and 39-50 ng·h/mL/100 mg. However, no marked increase of dose-normalized parameters of cromolyn was observed when increasing the SNAC dose from 400 to 1200 mg.

After administration of 80 mg of cromolyn combined with 600 mg of SNAC, all subjects reached the therapeutic level (i.e., at least 10 ng/mL) for at least 30 minutes. The therapeutic level was also reached in all subjects with 80/1200, 120/500 and 150/200 (mg/mg) cromolyn/SNAC combinations, but for less than 30 minutes in some subjects. With each of the other treatments, a few subjects failed to reached the therapeutic level.

SNAC absorption was not influenced by co-administration of cromolyn sodium. In view of its large inter-individual variability (CV between 42 and 94%), the SNAC peak absorption did not markedly diverge from dose-proportionality, with dose-normalized $C_{max}$ ranging from 4.09 to 7.20 µg/mL/1000 mg. For doses between 200 and 500 mg, the SNAC extent of absorption was also dose-proportional (dose-normalized $AUC_{(0-t)}$ between 2.58 and 2.79 µg·h/mL/1000 mg) but increased more than dose-proportionally for higher doses (from 3.30 to 5.05 µg·h/mL/1000 mg when SNAC doses were increased from 600 to 2000 mg).

This example shows that administration of SNAC with cromolyn clearly enhances the oral absorption of cromolyn. The best combination is 80 mg cromolyn administered with 600 mg SNAC, allowing all subjects to reach the 10-ng/mL therapeutic level for at least 30 minutes. All tested cromolyn sodium/SNAC combinations were well tolerated and did not produce any clinically relevant modifications of the clinical status of the subjects.

Example 5

In the previous example, the single dose study demonstrated that cromolyn was rapidly absorbed into the systemic circulations, reached maximum plasma concentrations at about 20 minutes post-dose and was rapidly cleared from the body within 6-8 hours with a mean elimination half-life of 1-2 hours. In addition, the cromolyn plasma concentration level was not influenced when the SNAC dose was reduced from 1200 to 600 mg. Based on the results of the single dose safety, tolerability and pharmacokinetics study shown in the previous example, wherein rapid clearance of cromolyn from the body indicated no accumulation of cromolyn would occur after multiple dosing of cromolyn, 80 mg cromolyn plus 600 mg SNAC twice a day dose was selected for a multiple dose study in healthy and allergic patients.

The purpose of this study was to evaluate the safety, tolerability, oral absorption, pharmacokinetics and pharmacodynamics following multiple dosing of oral cromolyn when given in combination with SNAC in healthy and allergic subjects. In order to be able to distinguish between cromolyn and other not-drug related issues, the study was placebo controlled. In order to evaluate the absorption of cromolyn, cromolyn was given with and without SNAC, a regimen that was expected to improve absorption of cromolyn. In order to evaluate the pharmacodynamics, it was important to compare the effect of cromolyn between healthy and allergic subjects (target population).

Accordingly, a double-blind, randomized, placebo-controlled, multiple dose study was conducted to evaluate the safety, tolerability, oral absorption, and pharmacokinetics of cromolyn when given as capsules twice daily for ten days in combination with SNAC. Additionally, the study was conducted to evaluate the effect of oral cromolyn on the wheal and flare reaction after intracutaneous injection of codeine and histamine in healthy male subjects. Thirdly, the study was conducted to evaluate the effect of cromolyn on the wheal and flare reaction after intracutaneous injection with an allergen in male subjects with allergies.

The volunteers were all males between 18 and 45 years of age, in good health, with a weight within 15% of normal range based upon Metropolitan Life Insurance Co. tables. All laboratory values (electrocardiogram, hematology, serum chemistries and urinalysis) obtained during screening were within normal ranges.

Two groups of human males were defined: group 1 consisted of 12 healthy male volunteers, and group 2 had 12 allergic male volunteers. Eight volunteers from each of Group 1 and 2 received 80 mg Cromolyn/600 mg SNAC; two volunteers from each group received 80 mg of Cromolyn/0 mg SNAC as a control and two volunteers from each group received controls of capsules with 0 mg Cromolyn/0 mg SNAC. The dosing regimen is illustrated in Table 7 below.

Cromolyn/SNAC capsule, Cromolyn control capsule, and placebo capsule formulations were prepared extemporaneously at the study site. The composition of the capsules varied, depending on the treatment administered. Each capsule containing the cromolyn/SNAC combination contained about 340 mg solids (SNAC and cromolyn sodium USP).

TABLE 7

Dosing regimen

| Number of subjects | Group 1 Per Dose, mg-Cromolyn/mg-SNAC | Group 2 Per Dose, mg-Cromolyn/mg-SNAC |
|---|---|---|
| 8 | 80/600 (2 capsules) | 80/600 (2 capsules) |
| 2 | 80/placebo (2 capsules) | 80/placebo (2 capsules) |
| 2 | Placebo (2 capsules) | Placebo (2 capsules) |

Each subject received oral dosing of the study medication twice a day for nine days. On the last day (i.e., day 10), only the morning dose was administered. The capsules were administered with up to 200 mL of water to the subjects in an upright position. The first dose of each day was administered following an overnight fast, and the second dose of each day was administered at least 1 hour before a meal or 4 hours after a meal. No food was allowed for at least 4 hours before the oral dosing.

Blood Samples for pharmacokinetics of cromolyn and SNAC (4.5 mL×2, one tube for cromolyn and one tube for SNAC, in chilled tri-sodium citrate tubes) were drawn in both treatment groups 15 minutes before the morning dose and at 20 minutes after the morning dose on days 2, 3, 4, 5, 6, 7, 8 and 9, and 15 minutes before the morning dose and at 5, 10, 15, 20, 30, and 45 minutes and 1, 1.5, 2, 3, 4, 6, and 8 hours after the morning dose on days 1 and 10.

From the literature there are indications that nasal and lung mast cells are more sensitive to cromolyn. Therefore, for the allergic subjects it was proposed to determine the effect of cromolyn/SNAC on symptoms generated by mast cell degranulation in the nasal mucosa induced by intranasal provocation with allergen. Healthy subjects received codeine/histamine to induce wheal and flare reaction, and allergic subjects received allergen/histamine to induce wheal and flare reaction.

Wheal and flare reaction was read 15 min. after the injections of codeine/histamine or allergen/histamine, traced by pen onto transparent cellophane and the length and width of the reaction was measured. Wheal and flare reaction was measured for Group 1 (healthy subjects) after intracutaneous injection of codeine/histamine before the morning dose on day 1, at 45 minutes after the morning dose on days 1, 2, 4, 6, 8 and 10, and at 4 and 8 hours after the morning dose on days 2, 4 and 10. Wheal and flare reaction was measured for Group 2 (subjects with allergies) after injection with allergen/histamine before the morning dose on day 1, at 60 minutes after the morning dose on days 4 and 10, and at 8 hours after the morning dose on day 4.

The allergic subjects in group 2 were also tested for response to allergen (pollen, trees, house dust mite, cats or dogs) using a nasal provocation test in which the allergen challenge vehicle was administered intranasally. The procedure was initiated by spraying dilution fluid (as was used for the allergen challenge; sodium hydrogen carbonate 2.5 mg, phenol 5 mg, sodium chloride 5 mg, HSA 0.3 mg in 1 ml water) into each nostril, followed 15 minutes later by spraying each nostril with one challenge puff, each 0.089 ml in volume of allergen at a concentration of 10.000 BU/mL. This resulted in a total dose of 1780 BU, 890 BU per nostril, which is considered a mild provocation.

The following assessments for nasal tolerability were made following allergen challenge: VAS scores and PNIF measurement (each time in triplicate). The nasal provocation test was performed at day −1 (baseline) and 60 min post dose on day 9. Nasal tolerability was assessed immediately before administration with vehicle and 15 min post vehicle challenge (=pre allergen challenge), and at 0.25, 0.5, 1.0, 1.5, 2.0, 2.5, 3.5, 4.5 and 23 hours post-challenge.

The criteria for evaluating pharmacokinetics were $C_{max}$, $T_{max}$, $AUC_{0-12}$, $AUC_{inf}$, $K_{el}$, $t_{1/2}$, MRT, CL/F, $V_d$/F of Cromolyn and SNAC. Pharmacodynamics were measured for Group 1 and 2 by measuring the length and width of the wheal and flare reaction, and permanent records were generated by marking on transparent tapes and/or by photographs. For Group 2 only, pharmacodynamics were also measured by VAS scores and PNIF measurements before and after nasal provocation test.

Pharmacokinetics

Figure 12:
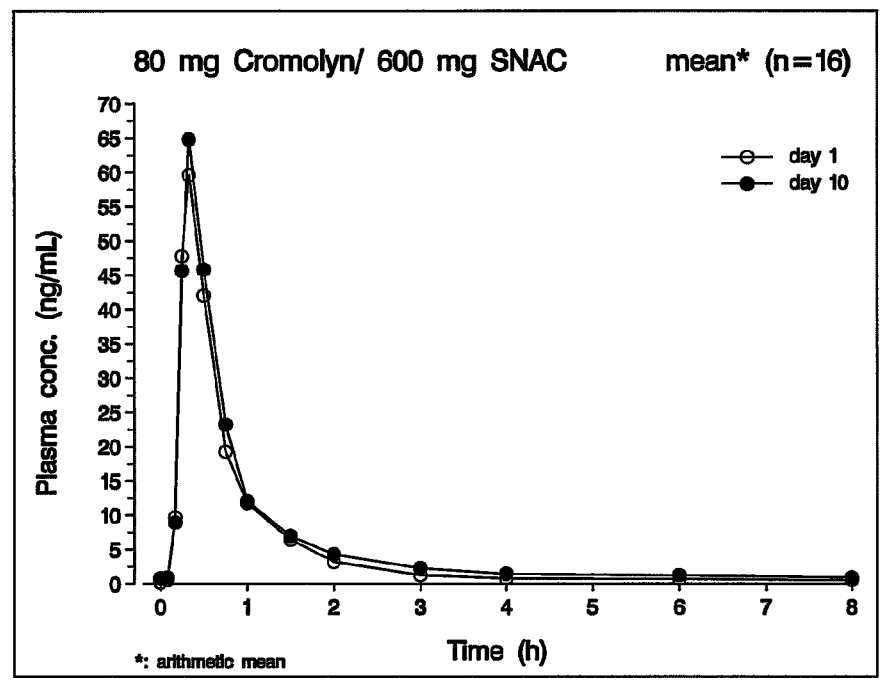
FIG. 12 depicts mean plasma concentration versus time profiles of cromolyn for Day 1 and Day 10 after an oral administration of a combination of cromolyn sodium and SNAC dosages.
Figure 13:
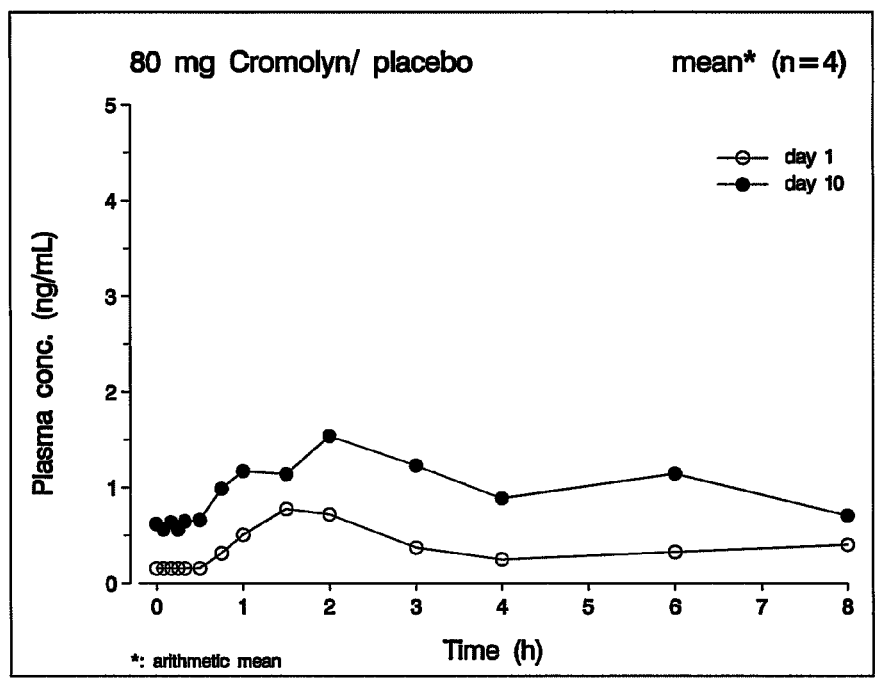
FIG. 13 depicts mean plasma concentration versus time profiles of cromolyn for Day 1 and Day 10 after an oral administration of a combination of cromolyn sodium and placebo.

Summary statistics for the pharmacokinetic parameters derived from plasma cromolyn for Day 1 and Day 10 are presented in Table 8 below. The mean plasma concentration versus time profile of cromolyn for Day 1 and Day 10 for 80 mg Cromolyn/600 mg SNAC is shown in FIG. 12, and the mean plasma concentration versus time profile of cromolyn for Day 1 and Day 10 for 80 mg Cromolyn/placebo is shown in FIG. 13.

TABLE 8

| Treatment | day | $C_{max}$ (ng/mL) | $T_{max}$ (h) | $AUC_{0-12}$ (ng·h/mL) mean (SD) | $AUC_{last}$ (ng·h/mL) | $AUC_{inf}$ (ng·h/mL) |
|---|---|---|---|---|---|---|
| 80 mg Cromolyn/600 mg SNAC N = 16 | 1 | 63.0 (41.2) | 0.34 (0.07) | 40.3 (26.4) | 39.7 (26.3) | 40.3 (26.4) |
|  | 10 | 71.3 (46.4) | 0.35 (0.10) | 48.8 (26.1) | — | — |
| 80 mg Cromolyn/placebo N = 3 | 1 | 1.1 (0.3) | 1.83 (0.29) | — | 4.7 (0.1)* | — |
|  | 10 | 2.3 (0.7) | 3.17 (2.47) | — | — | — |

*N = 2

As shown, cromolyn given orally in combination with SNAC was rapidly absorbed, with peak concentrations seen at approximately 20 minutes after drug administration in fasting male volunteers (allergic and healthy). Due to the short plasma half-life of the two compounds (cromolyn±45 min, SNAC±25 min), there was no accumulation during multiple dose treatment. In fact, plasma concentrations declined to negligible levels within 4 hour after each drug administration. The plasma-concentrations were almost back to zero after 4 hours, and there was no difference between $AUC_{0-12}$ and $AUC_{inf}$.

For subjects treated with Cromolyn combined with SNAC (N=16), the mean $C_{max}$ was somewhat higher on Day 10 than on Day 1. However, the between subject variability was large, which is also reflected in the large SD. When comparing the results on day 10 versus day 1, the within-subject variability appears to be less pronounced.

When cromolyn was administered without SNAC, the oral absorption was negligible (<2.3 ng/mL) and occurred. When cromolyn was given in combination with 600 mg SNAC, mean plasma concentrations of up to 65 ng/mL were reached.

Figure 14:
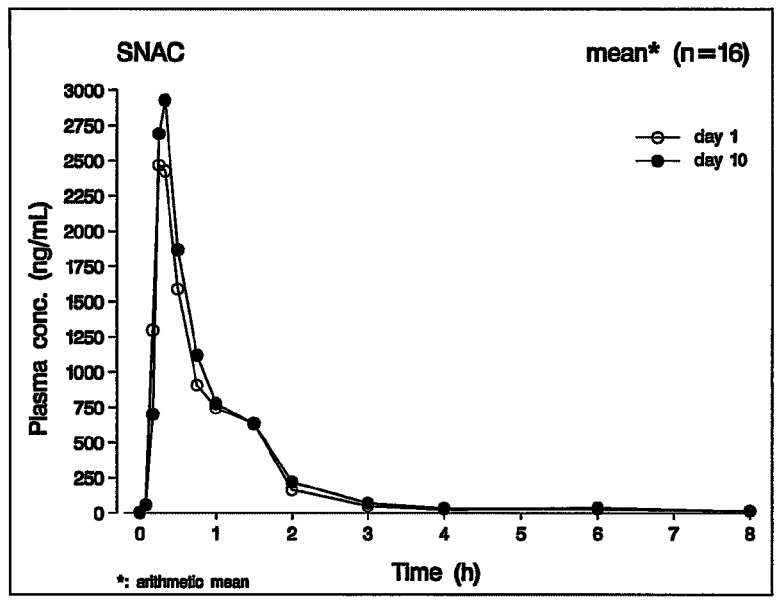
FIG. 14 depicts mean plasma concentration versus time profiles for SNAC for Day 1 and Day 10 after administration of a combination of cromolyn sodium and SNAC.

A summary of the descriptive statistics for pharmacokinetic parameters derived from plasma SNAC concentrations for Day 1 and Day 10 are presented in Table 9 below. Mean plasma concentrations-time data for SNAC for Day 1 and Day 10 after administration of 80 mg cromolyn/600 mg SNAC are shown in FIG. 14.

between variability of individual cromolyn concentrations was not due to the variability of SNAC concentration for the same subject. There was no direct relationship found between SNAC and cromolyn plasma concentrations on Day 1 and Day 10.

Pharmacodynamics

Figure 16:
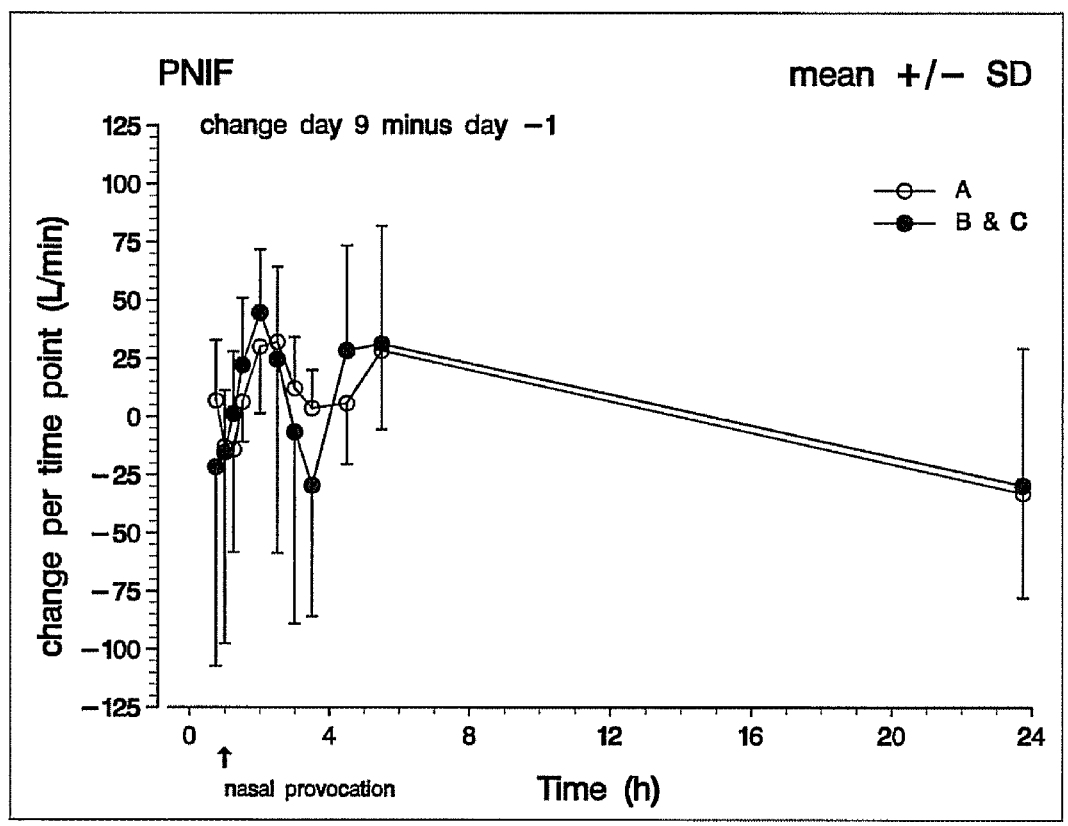
FIG. 16 shows the PNIF results as mean changes from baseline per time point (values on Day 9 minus the values on Day 1).

FIG. 16 shows the PNIF results as mean changes from baseline per time point (values on Day 9 minus the values on Day −1). For all subjects, a baseline wheal and flare reaction was found after challenge with codeine (healthy subjects) or with allergen (allergic subjects). However, the wheal and flare test for healthy subjects (codeine/histamine) and allergic subjects (allergen/histamine) did not show any treatment effect. Overall, both healthy and allergic subjects showed no clear change from baseline (pre-dose) for the wheal and flare skin reactions.

There were no apparent differences in mean change from baseline for PNIF scores (values on Day 9 minus the values on Day −1) between the treatments, obtained from the allergic subjects only. There was a smaller decrease of PNIF scores, for all treatments, after provocation on Day 9 than for Day −1 (shown as positive change from baseline in FIG. 16). There was also a large variation between subjects, and no difference was found between Cromolyn/SNAC and Cromolyn alone or placebo.

All subjects showed a change in VAS score after nasal provocation. However, the VAS scores were not influenced by

TABLE 9

Summary statistics of plasma SNAC pharmacokinetic parameters

| Treatment | day | $C_{max}$ (ng/mL) | $T_{max}$ (h) | $AUC_{0-12}$ (ng·h/mL) mean (SD) | $AUC_{last}$ (ng·h/mL) | $AUC_{inf}$ (ng·h/mL) |
|---|---|---|---|---|---|---|
| 80 mg Cromolyn/600 mg SNAC N = 16 | 1 | 2861 (2021) | 0.50 (0.37) | 2030 (567) | 2013 (563) | 2032 (568) |
|  | 10 | 3416 (1473) | 0.41 (0.32) | 2285 (692) | — | — |

The mean profiles for SNAC look rather similar for Day 1 and Day 10. For subjects treated with SNAC (N=16), the mean $C_{max}$ for SNAC was somewhat higher on Day 10 than on Day 1. The variation of SNAC concentration-time profiles was rather large between subjects. However, there was only limited within-subject variability (Day 10 versus Day 1).

$T_{max}$ was reached in about 30 minutes. The AUC was similar on Day 1 and Day 10.

Figure 15:
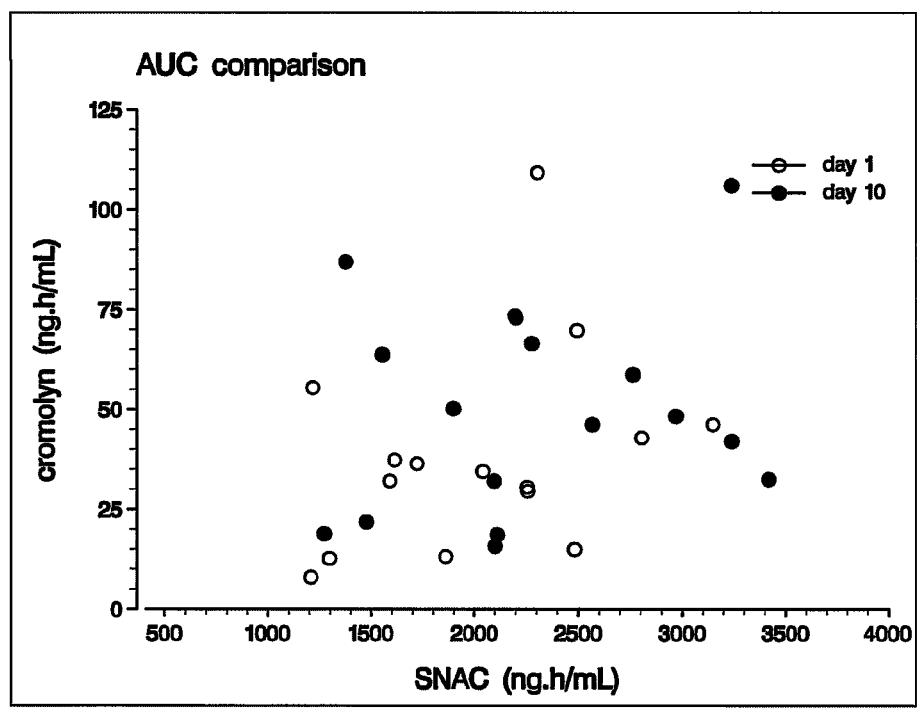
FIG. 15 depicts a correlation of the AUC values for plasma concentrations of SNAC and cromolyn.

After analysis of cromolyn and SNAC plasma concentrations, a large within and between subject variability in plasma SNAC and cromolyn concentrations was found. The correlation of individual SNAC versus cromolyn concentrations, shown in FIG. 15, shows that the relation for relative bioavailability between SNAC and cromolyn was weak, i.e. the large any of the treatments. The nose and throat were less sore after dosing with Cromolyn/SNAC. For the rest of the scales, no obvious differences in VAS scores were found before and after dosing with Cromolyn/SNAC.

CONCLUSIONS

It is clear that SNAC enhances the absorption of cromolyn when the two compounds are orally administered in combination. When cromolyn was administered alone, i.e., without SNAC, the oral absorption was practically negligible. Consequently, twice daily administration may not have been enough to achieve continuous exposure to cromolyn during the combined cromolyn/SNAC treatment, and this could explain why no clear effect of treatment could be observed for the pharmacodynamic parameters.

Between individuals, there was a large variation in the cromolyn and SNAC exposures in terms of AUC values. However, within individuals the variation was clearly less pronounced. The large plasma cromolyn concentration variability on the Day 2 to Day 9, measured at 20 min after dosing, is probably due to the large variability of $T_{max}$ between subjects.

There was no correlation found between the SNAC and Cromolyn plasma concentrations. The cromolyn relative bioavailability (AUC) seemed to vary independently of the plasma SNAC concentrations, i.e., the large variability for cromolyn in plasma cannot be explained by the variability in plasma SNAC concentrations.

For the wheal and flare reactions, the VAS scores and PNIF scores it can be firmly concluded that the challenge was indeed strong enough, since a clear effect was generated after each challenge that was administered, independent of group or treatment. The wheal and flare skin reactions were independent of treatment administered and did not clearly change from baseline (pre-dose). Apparently, oral cromolyn had no significant effects on skin mast cell degranulation when stimulated with codeine. However, the results show no apparent differences in mean change from baseline for PNIF scores (values on Day 9 minus the values on Day −1) between the treatments, obtained from the allergic subjects only.

For most VAS scores, the variability between subjects was too large to draw a general conclusion for this group. From the results of the nasal provocation test it was not possible to draw conclusions on the effect of Cromolyn/SNAC administration.

In this study, the wheal and flare reactions and the VAS scores were measured relatively soon after the challenge. This might be an explanation for the absence of clinically significant differences after cromolyn administration. An alternative explanation for the minimal effects of cromolyn on the pharmacodynamic parameters, despite significantly increased plasma levels compared to dosing without SNAC, might be that the achieved plasma levels were still too low to produce a local response to oral dosing with cromolyn. After inhalation of cromolyn, the local bioavailability of cromolyn is possibly much higher than the local bioavailability of cromolyn after oral dosing combined with SNAC.

As demonstrated by the data in the Examples and Figures, the use of compositions of the subject invention shows significant advantages for the delivery of biologically active agents.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. A method for treating a patient in need of treatment of an inflammatory disease, comprising administering to said patient an oral dosage form comprising:
   (a) cromolyn sodium; and
   (b) a delivery agent sodium N-[8-(2-hydroxybenzoyl) amino]caprylate (SNAC) that upon oral administration provides a systemic absorption of the cromolyn sodium in a physiologically effective amount, wherein the physiologically effective amount is enough to inhibit the release of histamine or cytokines or histamine and cytokines from mast cells,
   wherein the ratio of cromolyn sodium to the delivery agent is from 1:7.5 to 1:30 (weight/weight).

2. The method of claim 1 wherein the patient is a human.

3. The method of claim 1 wherein cromolyn sodium is in an amount from about 40 mg to about 1 g together with a delivery agent in an amount from about 100 mg to about 2500 mg.

4. The method of claim 1 wherein the inflammatory disease is allergic rhinitis, asthma, rheumatoid arthritis or an autoimmune disease.

5. The method of claim 1, wherein the $T_{max}$ for cromolyn sodium occurs at a time less than about 1 hour after oral administration.

6. The method of claim 1, wherein an AUC for cromolyn sodium of between about 16 and about 60 ng·h/mL is attained.

7. The method of claim 1, wherein a cromolyn sodium $C_{max}$ that is from about 10 to about 250 ng/mL is attained.

8. The method of claim 1 wherein the physiologically effective amount is enough to provide an absorption of cromolyn from the gastrointestinal tract of greater than about 3.5%, by weight, of the dose of cromolyn contained in the dosage form.

9. The method of claim 1 wherein the physiologically effective amount is enough to provide an absorption of cromolyn from the gastrointestinal tract of greater than about 2%, by weight, of the dose of cromolyn contained in the dosage form.

10. The method of claim 1, wherein the oral dosage form is in the form of a tablet, capsule or oral suspension.

11. The method of claim 1, wherein the oral dosage form is solid.

12. The method of claim 1, wherein the dose of cromolyn sodium is from about 40 mg to about 1 g.

13. The method of claim 12, wherein the dose of cromolyn sodium is from about 40 mg to about 240 mg.

14. The method of claim 12, wherein the dose of cromolyn sodium is from about 50 mg to about 150 mg.

15. The method of claim 1, wherein the dose of the delivery agent is from about 100 mg to about 1200 mg.

16. The method of claim 15, wherein the dose of the delivery agent is from about 200 mg to about 800 mg.

17. The method of claim 1, wherein said administration provides a $T_{max}$ for cromolyn sodium at about 0.1 to about 1.5 hours after oral administration.

18. The method of claim 17, wherein said administration provides a $T_{max}$ for cromolyn sodium at less than about 1 hours after oral administration.

19. The method of claim 17, wherein said administration provides a $T_{max}$ for cromolyn sodium at about 0.2 to about 0.5 hours after administration.

20. The method of claim 1, wherein said administration provides an AUC for cromolyn sodium of between about 15 and about 60 ng·h/mL.

21. The method of claim 20, wherein said administration provides an AUC for cromolyn sodium of between about 30 and about 40 ng·h/mL.

22. The method of claim 1, wherein said administration provides a cromolyn sodium $C_{max}$ from about 10 ng/ml to about 250 ng/ml.

23. The method of claim 22, wherein said administration provides a cromolyn sodium $C_{max}$ from about 20 to about 100 ng/mL.

24. The method of claim 22, wherein said administration provides a cromolyn sodium $C_{max}$ from about 40 to about 65 ng/mL.

25. The method of claim 22, wherein said administration provides a cromolyn sodium $C_{max}$ from about 20 to about 80 ng/mL within about 0.2 to about 1 hour after oral administration.

26. The method of claim 1, wherein the dose of cromolyn sodium is about 80 mg and the dose of delivery agent is about 600 mg.

27. The method of claim 1, wherein the ratio of cromolyn sodium to the delivery agent is 1:7.5 (weight/weight).

28. The method of claim 1, wherein the dose of cromolyn sodium and delivery agent is selected from the group consisting of about 40 mg cromolyn sodium and about 1200 mg delivery agent, about 80 mg cromolyn sodium and about 1200 mg delivery agent, and about 80 mg cromolyn sodium and about 600 mg delivery agent.

* * * * *